United States Patent
Vanslyke et al.

(10) Patent No.: US 10,335,075 B2
(45) Date of Patent: Jul. 2, 2019

(54) ADVANCED CALIBRATION FOR ANALYTE SENSORS

(71) Applicant: DexCom, Inc., San Diego, CA (US)

(72) Inventors: Stephen J. Vanslyke, Carlsbad, CA (US); Naresh C. Bhavaraju, San Diego, CA (US); Lucas Bohnett, San Diego, CA (US); Arturo Garcia, Chula Vista, CA (US); Apurv Ullas Kamath, San Diego, CA (US); Jack Pryor, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 550 days.

(21) Appl. No.: 13/827,119

(22) Filed: Mar. 14, 2013

(65) Prior Publication Data

US 2014/0278189 A1    Sep. 18, 2014

(51) Int. Cl.
  *A61B 5/1495* (2006.01)
  *G16H 40/40* (2018.01)

(52) U.S. Cl.
  CPC ........... *A61B 5/1495* (2013.01); *G16H 40/40* (2018.01)

(58) Field of Classification Search
  CPC .................... A61B 5/1495; G06F 19/3412
  See application file for complete search history.

(56) References Cited

U.S. PATENT DOCUMENTS

| | | | |
|---|---|---|---|
| 7,039,446 B2 | 5/2006 | Ruchti et al. | |
| 7,133,710 B2 | 11/2006 | Acosta et al. | |
| 7,299,080 B2 | 11/2007 | Acosta et al. | |
| 7,920,906 B2 | 4/2011 | Goode et al. | |
| 8,062,249 B2 | 11/2011 | Wilinska et al. | |
| 8,103,456 B2 | 1/2012 | Doniger et al. | |
| 8,346,335 B2 | 1/2013 | Harper et al. | |
| 2002/0161288 A1 | 10/2002 | Shin et al. | |
| 2003/0147078 A1 | 8/2003 | Zirk et al. | |
| 2003/0235817 A1 | 12/2003 | Bartkowiak et al. | |
| 2010/0057042 A1 | 3/2010 | Hayter | |
| 2010/0069730 A1 | 3/2010 | Bergstrom et al. | |
| 2010/0168545 A1 | 7/2010 | Kamath et al. | |

(Continued)

FOREIGN PATENT DOCUMENTS

| EP | 0404562 B1 | 8/1998 |
|---|---|---|
| EP | 1467652 B1 | 7/2009 |

(Continued)

OTHER PUBLICATIONS

STIC Search Report dated Feb. 15, 2018.*
Wang et al., Metal Oxide Gas Sensors Sensitivity and Influencing Factors. Sensors 2010, Mar. 15, 2010.*

*Primary Examiner* — Kyle R Quigley
(74) *Attorney, Agent, or Firm* — Knobbe Martens Olson & Bear, LLP

(57) ABSTRACT

Systems and methods for processing sensor data and calibration of the sensors are provided. In some embodiments, the method for calibrating at least one sensor data point from an analyte sensor comprises receiving a priori calibration distribution information; receiving one or more real-time inputs that may influence calibration of the analyte sensor; forming a posteriori calibration distribution information based on the one or more real-time inputs; and converting, in real-time, at least one sensor data point calibrated sensor data based on the a posteriori calibration distribution information.

20 Claims, 22 Drawing Sheets

(56) References Cited

U.S. PATENT DOCUMENTS

| | | | |
|---|---|---|---|
| 2010/0168546 A1* | 7/2010 | Kamath | A61B 5/0031 600/365 |
| 2010/0191472 A1 | 7/2010 | Doniger et al. | |
| 2010/0230285 A1 | 9/2010 | Hoss et al. | |
| 2010/0280441 A1 | 11/2010 | Wilinska et al. | |
| 2011/0077494 A1 | 3/2011 | Doniger et al. | |
| 2011/0237917 A1 | 9/2011 | Roy et al. | |
| 2012/0010600 A1 | 1/2012 | Wilinska et al. | |
| 2012/0123234 A1 | 5/2012 | Atlas et al. | |
| 2012/0123691 A1 | 5/2012 | Doniger et al. | |
| 2012/0191362 A1 | 7/2012 | Schmitt et al. | |
| 2012/0265037 A1* | 10/2012 | Bohm | G01N 27/3274 600/309 |
| 2013/0030841 A1 | 1/2013 | Bergstrom et al. | |
| 2013/0060112 A1 | 3/2013 | Pryor et al. | |

FOREIGN PATENT DOCUMENTS

| | | |
|---|---|---|
| EP | 1489961 B1 | 9/2010 |
| EP | 1702561 B1 | 5/2011 |
| EP | 2079358 B1 | 8/2011 |
| EP | 2205148 B1 | 10/2011 |
| EP | 2529783 A1 | 12/2012 |
| EP | 2551784 A1 | 1/2013 |
| EP | 2561807 A1 | 2/2013 |
| WO | WO 2003/063699 | 8/2003 |
| WO | WO 2003/076883 | 9/2003 |
| WO | WO 2003/082098 | 10/2003 |
| WO | WO 2005/065542 | 7/2005 |
| WO | WO 2005/099567 | 10/2005 |
| WO | WO 2007/027843 | 3/2007 |
| WO | WO 2007/112034 | 10/2007 |
| WO | WO 2010/088568 | 8/2010 |
| WO | WO 2010/097796 | 9/2010 |
| WO | WO 2010/099507 | 9/2010 |
| WO | WO 2010/114929 | 10/2010 |
| WO | WO 2011/022362 | 2/2011 |
| WO | WO 2011/119201 | 9/2011 |
| WO | WO 2012/108398 | 8/2012 |
| WO | WO 2012/122462 | 9/2012 |
| WO | WO 2013/063527 | 5/2013 |

* cited by examiner

ADVANCED CALIBRATION FOR ANALYTE SENSORS

TECHNICAL FIELD

The embodiments described herein relate generally to systems and methods for processing sensor data from continuous analyte sensors and for calibration of the sensors.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricks to obtain blood samples for measurement. Due to the lack of comfort and convenience associated with finger pricks, a person with diabetes normally only measures his or her glucose levels two to four times per day. Unfortunately, time intervals between measurements can be spread far enough apart that the person with diabetes finds out too late of a hyperglycemic or hypoglycemic condition, sometimes incurring dangerous side effects. It is not only unlikely that a person with diabetes will take a timely SMBG value, it is also likely that he or she will not know if his or her blood glucose value is going up (higher) or down (lower) based on conventional methods. Diabetics thus may be inhibited from making educated insulin therapy decisions.

Another device that some diabetics use to monitor their blood glucose is a continuous analyte sensor. A continuous analyte sensor typically includes a sensor that is placed subcutaneously, transdermally (e.g., transcutaneously), or intravascularly. The sensor measures the concentration of a given analyte within the body, and generates a raw signal that is transmitted to electronics associated with the sensor. The raw signal is converted into an output value that is displayed on a display. The output value that results from the conversion of the raw signal is typically expressed in a form that provides the user with meaningful information, such as blood glucose expressed in mg/dL.

SUMMARY

The present systems and methods relate to processing analyte sensor data. The various embodiments of the present systems and methods for processing analyte sensor data have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

One aspect of the present embodiments includes the realization that, with some sensors, it becomes desirable to adjust distributions of sensitivity and/or baseline. Some conventional continuous glucose monitoring data processing relies on the assumption that blood glucose inputs (e.g., assuming they pass certain outlier criteria) are accurate. For example, the calibration parameters are estimated with least-squares regression that assumes there are no errors in the reference values. In contrast, some of the disclosed embodiments recognize that the blood glucose inputs may be neither right nor wrong, but rather represent a range of possible values (including erroneous values), and may be beneficial to adjust the distribution of sensitivity and/or baseline.

One aspect of the present embodiments includes the realization that, with some sensors, it becomes desirable to employ adaptive boundaries for sensitivity and/or baseline. Some conventional calibration checks include the use of upper and/or lower boundaries to discern whether the calibrated data falls within an acceptable range or zone. These upper and lower boundaries may be a priori information and may be used to guide or validate the baseline (b) and/or sensitivity (m) determined from the regression analysis. This can be useful in situations wherein regression results in errant sensitivity or baseline values. For example, when points (matched pairs) used for regression are too close in their reference values (i.e. not enough glucose range in the calibration), the resulting regression statistically is less accurate than when the values are spread farther apart. As another example, a sensor that is not properly deployed or is damaged during deployment can yield a skewed or errant baseline signal. It is thus beneficial to be able to compensate for less-statistically accurate regressions by employing adaptive boundaries, and to identify improper deployment of or damage to a sensor by analysis of baseline signal.

One aspect of the present embodiments includes the realization that, with some sensors, it becomes desirable to increase or decrease reliance on blood glucose input based on a level of certainty. Some conventional continuous glucose monitoring data processing relies on the assumption that factory calibration information is accurate. However, it is known that over the life of a sensor, the sensor may begin to show signs of use and/or wear. For example, it has been found that a sensor's sensitivity to analyte concentration during a sensor session may change or drift as a function of time, and it can be beneficial to compensate for this by adjusting reliance on blood glucose input.

One aspect of the present embodiments includes the realization that, with some sensors, it becomes desirable to employ a Bayesian Learning Approach for Drift Estimation and Correction. Sensors can be manufactured with glucose sensitivity of a predetermined value and/or within a predetermined range, which may be determined from an in vitro test by the manufacturer. The sensor design can exhibit a characteristic sensitivity profile; namely, after sensor insertion, the sensors begin at an initial sensitivity that is higher than the in vitro sensitivity because of changes in the sensor properties after insertion, after which this sensitivity increases and reaches a steady state value between days 4 and 7 (post sensor insertion), and it can be desirable to compensate for drift by utilizing selected strategies as described herein.

In a first aspect, a method is provided for calibrating at least one sensor data point from an analyte sensor, the method comprising: receiving a priori calibration distribution information; receiving one or more real-time inputs that may influence calibration of the analyte sensor; forming a posteriori calibration distribution information based on the one or more real-time inputs; and converting, in real-time, at least one sensor data point calibrated sensor data based on the a posteriori calibration distribution information.

In an embodiment of the first aspect, which is generally applicable, particularly with any other embodiment of the first aspect, the a priori calibration distribution information comprises information from previous calibrations of a particular sensor session and/or information obtained prior to sensor insertion.

In an embodiment of the first aspect, which is generally applicable, particularly with any other embodiment of the first aspect, the a priori calibration distribution information comprises probability distributions for sensitivity (m), sensitivity-related information, baseline (b), or baseline-related information.

In an embodiment of the first aspect, which is generally applicable, particularly with any other embodiment of the first aspect, the a priori calibration distribution information comprises a priori guidance or validation ranges.

In an embodiment of the first aspect, which is generally applicable, particularly with any other embodiment of the first aspect, the one or more real-time inputs comprise data received or determined since a previous calibration process. The one or more real-time inputs comprises, in certain embodiments, at least one of: internally-derived real-time data, externally-derived real-time data, and combinations of internally- and externally-derived real-time data. Internally-derived real-time data, in certain embodiments, includes at least one type of information selected from the group consisting of: stimulus signal output of sensor; sensor data measured by the sensor indicative of an analyte concentration; sensor data indicative of analyte rate-of-change; temperature measurements; sensor data from multi-electrode sensors; sensor data generated by redundant sensors; sensor data generated by one or more auxiliary sensors; data representative of a pressure on sensor; data generated by an accelerometer; sensor diagnostic information; impedance; and certainty level. Externally-derived real-time data, in certain embodiments, includes at least one type of information selected from the group consisting of: glucose concentration information obtained from a reference monitor; information related to meal; insulin dosing time and amounts; insulin estimates; exercise; sleep; illness; stress; hydration; and hormonal conditions. Combinations of internally- and externally-derived real-time data, in certain embodiments, includes at least one type of information selected from the group consisting of: information gathered from population based data; glucose concentration of the host; error at calibration or error in matched data pair; site of sensor implantation specific relationships; time since sensor manufacture; exposure of sensor to temperature, humidity, external factors, on shelf; a measure of noise in an analyte concentration signal; and a level of certainty.

In an embodiment of the first aspect, which is generally applicable, particularly with any other embodiment of the first aspect, the method further comprises determining a level of certainty associated with the calibration information and/or calibrated sensor data.

In an embodiment of the first aspect, which is generally applicable, particularly with any other embodiment of the first aspect, forming a posteriori calibration distribution information comprises at least one of: 1) an adjustment of the a priori calibration distribution information or 2) a creation of a new range or distribution information based on the one or more real-time inputs. An adjustment of the a priori calibration distribution information, in certain embodiments, comprises shifting, tightening, or loosening the a priori calibration distribution.

In an embodiment of the first aspect, which is generally applicable, particularly with any other embodiment of the first aspect, the calibration distribution information is selected from the group consisting of: sensitivity; change in sensitivity; rate of change of sensitivity; baseline; change in baseline, rate of change of baseline, baseline profile associated with the sensor; sensitivity profile associated with the sensor; linearity; response time; relationships between properties of the sensor; relationships between particular stimulus signal output; and patient specific relationships between sensor and sensitivity, baseline, drift, impedance, impedance/temperature relationship, site of sensor implantation.

In an embodiment of the first aspect, which is generally applicable, particularly with any other embodiment of the first aspect, the method further comprises providing output of calibrated sensor data.

In an embodiment of the first aspect, which is generally applicable, particularly with any other embodiment of the first aspect, the method is implemented on a computer having a processor and a memory coupled to said processor, wherein at least one of steps (a) through (e) are performed using said processor.

In an embodiment of the first aspect, the above embodiments may be combined in any way. That is, any two, three or more of the embodiments for calibrating at least one sensor data point from an analyte sensor may be combined.

In a second aspect, a system for calibrating at least one sensor data point from a continuous analyte sensor, the system comprising sensor electronics configured to be operably connected to a continuous analyte sensor, the sensor electronics configured to: receive a priori calibration distribution information; receive one or more real-time inputs that may influence calibration of the analyte sensor; form a posteriori calibration distribution information using the one or more real-time inputs; and convert, in real-time, at least one sensor data point calibrated sensor data based on the a posteriori calibration distribution information.

In an embodiment of the second aspect, which is generally applicable, the sensor electronics comprise a processor module, the processor module comprising instructions stored in computer memory, wherein the instructions, when executed by the processor module, cause the sensor electronics to perform the forming and the determining.

In a third aspect, a system for calibrating at least one sensor data point from an analyte sensor, the system comprising: means for receiving a priori calibration distribution information; means for receiving one or more real-time inputs that may influence calibration of the analyte sensor; means for forming a posteriori calibration distribution information based on the one or more real-time inputs; and means for converting, in real-time, at least one sensor data point calibrated sensor data based on the a posteriori calibration distribution information.

In further aspects and embodiments, the above method features of the first aspect are formulated in terms of a system, as in, e.g., the second or third aspects, having the analyte sensor and control means configured to carry out the method features. Any of the features of an embodiment of the first, second, or third aspects is applicable to all aspects and embodiments identified herein. Moreover, any of the features of an embodiment of the first, second, or third aspects is independently combinable, partly or wholly with other embodiments described herein in any way, e.g., one, two, or three or more embodiments may be combinable in whole or in part. Further, any of the features of an embodiment of the first, second, or third aspects may be made optional to other aspects or embodiments. Any aspect or embodiment of a method can be performed by a system or apparatus of another aspect or embodiment, and any aspect or embodiment of a system can be configured to perform a method of another aspect or embodiment.

BRIEF DESCRIPTION OF THE DRAWINGS

The details of the present disclosure, both as to its structure and operation, may be understood in part by study of the accompanying drawings, in which like reference numerals refer to like parts. The drawings are not necessarily to scale, emphasis instead being placed upon illustrating the principles of the disclosure.

DETAILED DESCRIPTION

Definitions

Figure 1:
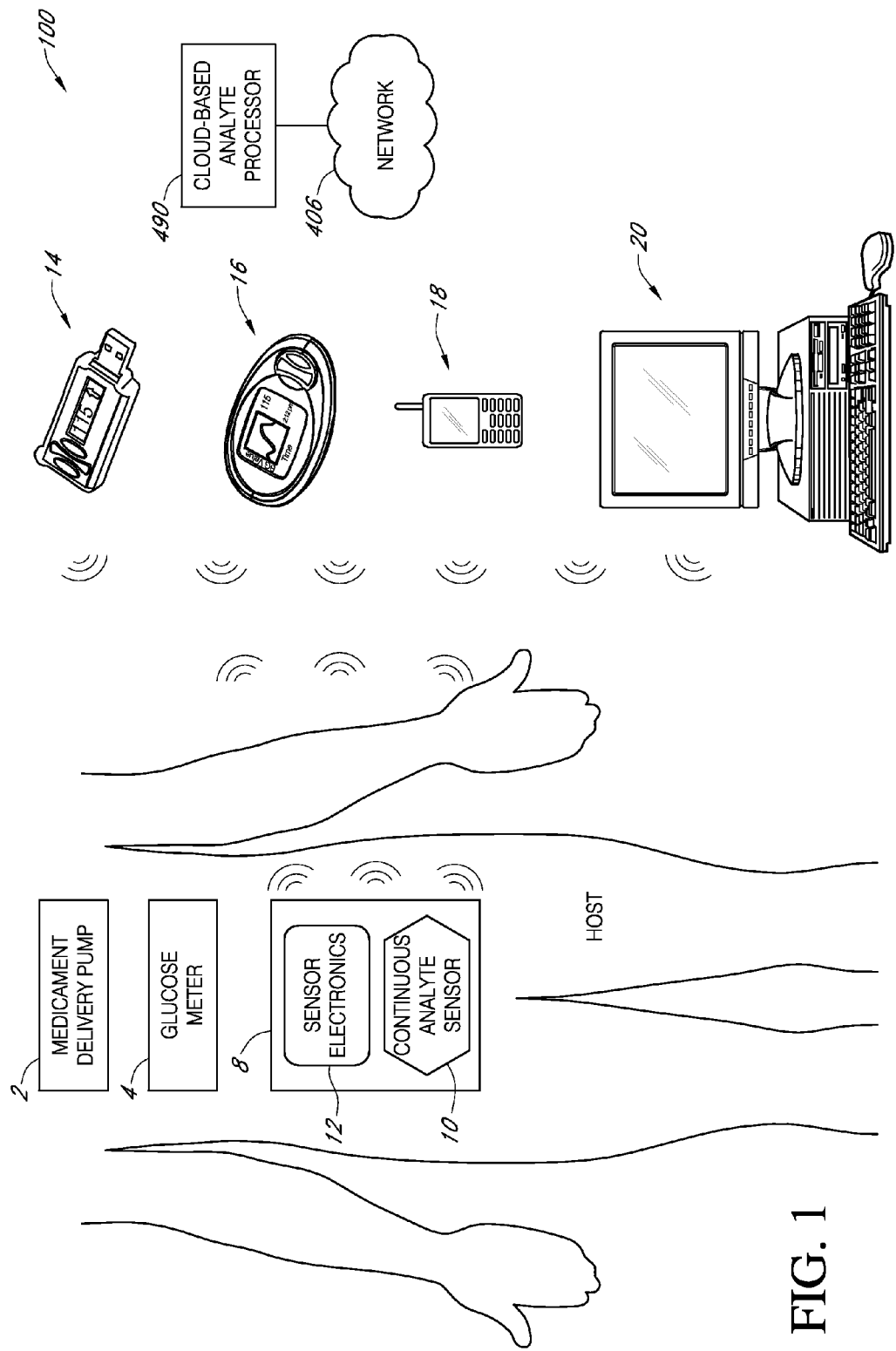
FIG. 1 is a schematic view of a continuous analyte sensor system attached to a host and communicating with a plurality of example devices.

In order to facilitate an understanding of the embodiments described herein, a number of terms are defined below.

The term "analyte," as used herein, is a broad term, and is to be given its ordinary and customary meaning to a person of ordinary skill in the art (and is are not to be limited to a special or customized meaning), and refers without limitation to a substance or chemical constituent in a biological fluid (for example, blood, interstitial fluid, cerebral spinal fluid, lymph fluid or urine) that can be analyzed. Analytes may include naturally occurring substances, artificial substances, metabolites, and/or reaction products. In some embodiments, the analyte for measurement by the devices, and methods disclosed herein is glucose.

The terms "continuous analyte sensor," and "continuous glucose sensor," as used herein, are broad terms, and are to be given their ordinary and customary meaning to a person of ordinary skill in the art (and are not to be limited to a special or customized meaning), and refer without limitation to a device that continuously or continually measures a concentration of an analyte/glucose and/or calibrates the device (e.g., by continuously or continually adjusting or determining the sensor's sensitivity and background), for example, at time intervals ranging from fractions of a second up to, for example, 1, 2, or 5 minutes, or longer.

The terms "raw data stream" and "data stream," as used herein, are broad terms, and are to be given their ordinary and customary meaning to a person of ordinary skill in the art (and are not to be limited to a special or customized meaning), and refer without limitation to an analog or digital signal directly related to the analyte concentration measured by the analyte sensor. In one example, the raw data stream is digital data in counts converted by an A/D converter from an analog signal (for example, voltage or amps) representative of an analyte concentration. The terms broadly encompass a plurality of time spaced data points from a substantially continuous analyte sensor, which comprises individual measurements taken at time intervals ranging from fractions of a second up to, for example, 1, 2, or 5 minutes or longer.

The terms "sensor data," as used herein is a broad term and is to be given its ordinary and customary meaning to a person of ordinary skill in the art (and are not to be limited to a special or customized meaning), and furthermore refers without limitation to any data associated with a sensor, such as a continuous analyte sensor. Sensor data includes a raw data stream, or simply data stream, of analog or digital signal directly related to a measured analyte from an analyte sensor (or other signal received from another sensor), as well as calibrated and/or filtered raw data. In one example, the sensor data comprises digital data in "counts" converted by an A/D converter from an analog signal (e.g., voltage or amps) and includes one or more data points representative of a glucose concentration. Thus, the terms "sensor data point" and "data point" refer generally to a digital representation of sensor data at a particular time. The terms broadly encompass a plurality of time spaced data points from a sensor, such as a from a substantially continuous glucose sensor, which comprises individual measurements taken at time intervals ranging from fractions of a second up to, e.g., 1, 2, or 5 minutes or longer. In another example, the sensor data includes an integrated digital value representative of one or more data points averaged over a time period. Sensor data may include calibrated data, smoothed data, filtered data, transformed data, and/or any other data associated with a sensor.

The term "counts," as used herein, is a broad term, and is to be given its ordinary and customary meaning to a person of ordinary skill in the art (and is not to be limited to a special or customized meaning), and refers without limitation to a unit of measurement of a digital signal. In one example, a raw data stream measured in counts is directly related to a voltage (for example, converted by an A/D converter), which is directly related to current from a working electrode.

The term "matched data pair" or "data pair" as used herein is a broad term and is to be given its ordinary and customary meaning to a person of ordinary skill in the art (and is not to be limited to a special or customized meaning), and furthermore refers without limitation to reference data (for example, one or more reference analyte data points) matched with substantially time corresponding sensor data (for example, one or more sensor data points).

The term "sensor electronics," as used herein, is a broad term, and is to be given its ordinary and customary meaning to a person of ordinary skill in the art (and is not to be limited to a special or customized meaning), and refers without limitation to the components (for example, hardware and/or software) of a device configured to process data.

The term "calibration" as used herein is a broad term, and is to be given its ordinary and customary meaning to a person of ordinary skill in the art (and is not to be limited to a special or customized meaning), and refers without limitation to the process of determining the relationship between raw sensor data (e.g., analog (nA) or digital units (counts) to clinically meaningful units (e.g., mg/dl or mmol/L for glucose)).

The terms "calibrated data" and "calibrated data stream" as used herein are broad terms and are to be given their ordinary and customary meaning to a person of ordinary skill in the art (and are not to be limited to a special or customized meaning), and furthermore refer without limitation to data that has been transformed from its raw state to another state using a function, for example a transformation function, to provide a meaningful value to a user.

The term "calibration set" as used herein is a broad term, and is to be given its ordinary and customary meaning to a person of ordinary skill in the art (and is not to be limited to a special or customized meaning), and refers without limitation to a set of data comprising information useful for calibration. In some embodiments, the calibration set is formed from one or more matched data pairs, which are used to determine the relationship between the reference data and the sensor data; however other data derived pre-implant, externally or internally may also be used.

The terms "sensitivity" or "sensor sensitivity," as used herein, are broad terms, and are to be given their ordinary and customary meaning to a person of ordinary skill in the art (and is not to be limited to a special or customized meaning), and refer without limitation to an amount of signal produced by a certain concentration of a measured analyte, or a measured species (e.g., $H_2O_2$) associated with the measured analyte (e.g., glucose). For example, in one embodiment, a sensor has a sensitivity of from about 1 to about 300 picoAmps of current for every 1 mg/dL of glucose analyte.

The terms "sensitivity profile" or "sensitivity curve," as used herein, are broad terms, and are to be given their ordinary and customary meaning to a person of ordinary skill in the art (and is not to be limited to a special or customized meaning), and refer without limitation to a representation of a change in sensitivity over time.

Overview

Conventional in vivo continuous analyte sensing technology has typically relied on reference measurements performed during a sensor session for calibration of the continuous analyte sensor. The reference measurements are matched with substantially time corresponding sensor data to create matched data pairs. Regression is then performed on the matched data pairs (e.g., by using least squares regression) to generate a conversion function that defines a relationship between a sensor signal and an estimated glucose concentration.

In critical care settings, calibration of continuous analyte sensors is often performed by using, as reference, a calibration solution with a known concentration of the analyte. This calibration procedure can be cumbersome, as a calibration bag, separate from (and an addition to) an IV (intravenous) bag, is typically used. In the ambulatory setting, calibration of continuous analyte sensors has traditionally been performed by capillary blood glucose measurements (e.g., a finger stick glucose test), through which reference data is obtained and input into the continuous analyte sensor system. This calibration procedure typically involves frequent finger stick measurements, which can be inconvenient and painful.

Heretofore, systems and methods for in vitro calibration of a continuous analyte sensor by the manufacturer (e.g., factory calibration), without reliance on periodic recalibration, have for the most part been inadequate with respect to high levels of sensor accuracy required for glycemic management. Part of this can be attributed to changes in sensor properties (e.g., sensor sensitivity) that can occur during sensor use. Thus, calibration of continuous analyte sensors has typically involved periodic inputs of reference data, whether they are associated with a calibration solution or with a finger stick measurement. This can be very burdensome to the patient in the ambulatory setting or the hospital staff in the critical care setting.

Described herein are systems methods for calibrating continuous analyte sensors that are capable of achieving high levels of accuracy, without (or with reduced) reliance on reference data from a reference analyte monitor (e.g., from a blood glucose meter).

Sensor System

FIG. 1 depicts an example system 100, in accordance with some example implementations. The system 100 includes a continuous analyte sensor system 8 including sensor electronics 12 and a continuous analyte sensor 10. The system 100 may include other devices and/or sensors, such as medicament delivery pump 2 and glucose meter 4. The continuous analyte sensor 10 may be physically connected to sensor electronics 12 and may be integral with (e.g., non-releasably attached to) or releasably attachable to the continuous analyte sensor 10. The sensor electronics 12, medicament delivery pump 2, and/or glucose meter 4 may couple with one or more devices, such as display devices 14, 16, 18, and/or 20.

In some example implementations, the system 100 may include a cloud-based analyte processor 490 configured to analyze analyte data (and/or other patient related data) provided via network 406 (e.g., via wired, wireless, or a combination thereof) from sensor system 8 and other devices, such as display devices 14-20 and the like, associated with the host (also referred to as a patient) and generate reports providing high-level information, such as statistics, regarding the measured analyte over a certain time frame. A full discussion of using a cloud-based analyte processing system may be found in U.S. patent application Ser. No. 13/788,375, entitled "Cloud-Based Processing of Analyte Data" and filed on Mar. 7, 2013, herein incorporated by reference in its entirety.

In some example implementations, the sensor electronics 12 may include electronic circuitry associated with measuring and processing data generated by the continuous analyte sensor 10. This generated continuous analyte sensor data may also include algorithms, which can be used to process and calibrate the continuous analyte sensor data, although these algorithms may be provided in other ways as well. The sensor electronics 12 may include hardware, firmware, software, or a combination thereof to provide measurement of levels of the analyte via a continuous analyte sensor, such as a continuous glucose sensor. An example implementation of the sensor electronics 12 is described further below with respect to FIG. 2.

The sensor electronics 12 may, as noted, couple (e.g., wirelessly and the like) with one or more devices, such as display devices 14, 16, 18, and/or 20. The display devices 14, 16, 18, and/or 20 may be configured for presenting information (and/or alarming), such as sensor information transmitted by the sensor electronics 12 for display at the display devices 14, 16, 18, and/or 20.

The display devices may include a relatively small, key fob-like display device 14, a relatively large, hand-held display device 16, a cellular phone 18 (e.g., a smart phone, a tablet, and the like), a computer 20, and/or any other user equipment configured to at least present information (e.g., medicament delivery information, discrete self-monitoring glucose readings, heart rate monitor, caloric intake monitor, and the like).

In some example implementations, the relatively small, key fob-like display device 14 may comprise a wrist watch, a belt, a necklace, a pendent, a piece of jewelry, an adhesive patch, a pager, a key fob, a plastic card (e.g., credit card), an identification (ID) card, and/or the like. This small display device 14 may include a relatively small display (e.g., smaller than the large display device 16) and may be configured to display certain types of displayable sensor information, such as a numerical value and an arrow.

In some example implementations, the relatively large, hand-held display device 16 may comprise a hand-held receiver device, a palm-top computer, and/or the like. This large display device may include a relatively larger display (e.g., larger than the small display device 14) and may be configured to display information, such as a graphical representation of the continuous sensor data including current and historic sensor data output by sensor system 8.

In some example implementations, the continuous analyte sensor 10 comprises a sensor for detecting and/or measuring analytes, and the continuous analyte sensor 10 may be configured to continuously detect and/or measure analytes as a non-invasive device, a subcutaneous device, a transdermal device, and/or an intravascular device. In some example implementations, the continuous analyte sensor 10 may analyze a plurality of intermittent blood samples, although other analytes may be used as well.

In some example implementations, the continuous analyte sensor 10 may comprise a glucose sensor configured to measure glucose in the blood or interstitial fluid using one or more measurement techniques, such as enzymatic, chemical, physical, electrochemical, spectrophotometric, polarimetric, calorimetric, iontophoretic, radiometric, immunochemical, and the like. In implementations in which the continuous analyte sensor 10 includes a glucose sensor, the glucose sensor may be comprise any device capable of measuring the concentration of glucose and may use a variety of techniques to measure glucose including invasive, minimally invasive, and non-invasive sensing techniques (e.g., fluorescence monitoring), to provide a data, such as a data stream, indicative of the concentration of glucose in a host. The data stream may be sensor data (raw and/or filtered), which may be converted into a calibrated data stream used to provide a value of glucose to a host, such as a user, a patient, or a caretaker (e.g., a parent, a relative, a guardian, a teacher, a doctor, a nurse, or any other individual that has an interest in the wellbeing of the host). Moreover, the continuous analyte sensor 10 may be implanted as at least one of the following types of sensors: an implantable glucose sensor, a transcutaneous glucose sensor, implanted in a host vessel or extracorporeally, a subcutaneous sensor, a refillable subcutaneous sensor, an intravascular sensor.

Although the disclosure herein refers to some implementations that include a continuous analyte sensor 10 comprising a glucose sensor, the continuous analyte sensor 10 may comprises other types of analyte sensors as well. Moreover, although some implementations refer to the glucose sensor as an implantable glucose sensor, other types of devices capable of detecting a concentration of glucose and providing an output signal representative of glucose concentration may be used as well. Furthermore, although the description herein refers to glucose as the analyte being measured, processed, and the like, other analytes may be used as well including, for example, ketone bodies (e.g., acetone, acetoacetic acid and beta hydroxybutyric acid, lactate, etc.), glucagon, acetyl-CoA, triglycerides, fatty acids, intermediaries in the citric acid cycle, choline, insulin, cortisol, testosterone, and the like.

Figure 2:
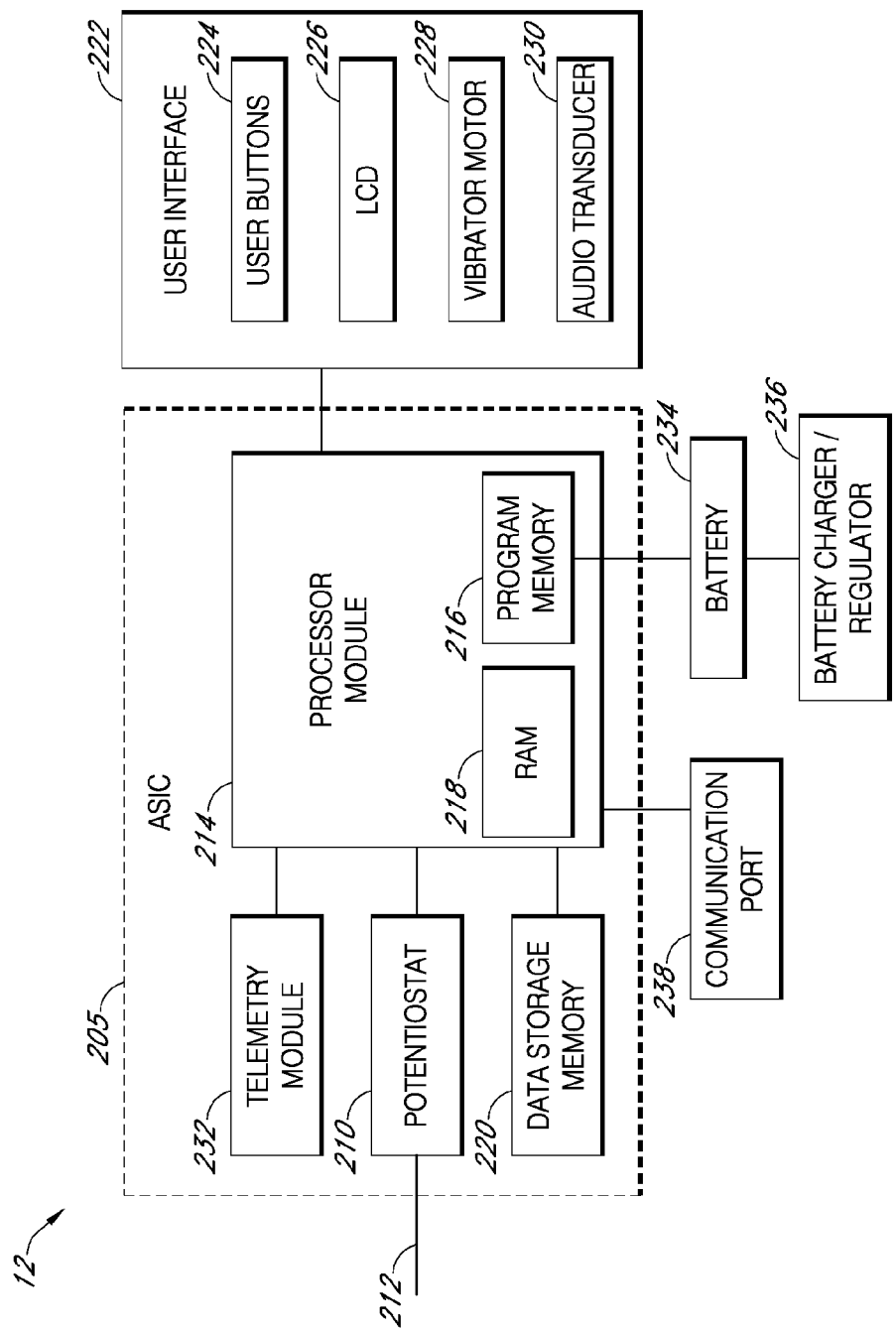
FIG. 2 is a block diagram that illustrates electronics associated with the sensor system of FIG. 1.

FIG. 2 depicts an example of sensor electronics 12, in accordance with some example implementations. The sensor electronics 12 may include sensor electronics that are configured to process sensor information, such as sensor data, and generate transformed sensor data and displayable sensor information, e.g., via a processor module. For example, the processor module may transform sensor data into one or more of the following: filtered sensor data (e.g., one or more filtered analyte concentration values), raw sensor data, calibrated sensor data (e.g., one or more calibrated analyte concentration values), rate of change information, trend information, rate of acceleration/deceleration information, sensor diagnostic information, location information, alarm/alert information, calibration information, smoothing and/or filtering algorithms of sensor data, and/or the like.

In some embodiments, a processor module 214 is configured to achieve a substantial portion, if not all, of the data processing. Processor module 214 may be integral to sensor electronics 12 and/or may be located remotely, such as in one or more of devices 14, 16, 18, and/or 20 and/or cloud 490. In some embodiments, processor module 214 may comprise a plurality of smaller subcomponents or submodules. For example, processor module 214 may include an alert module (not shown) or prediction module (not shown), or any other suitable module that may be utilized to efficiently process data. When processor module 214 is made up of a plurality of submodules, the submodules may be located within processor module 214, including within the sensor electronic 12 or other associated devices (e.g., 14, 16, 18, 20 and/or 490). For example, in some embodiments, processor module 214 may be located at least partially within cloud-based analyte processor 490 or elsewhere in network 406.

In some example implementations, the processor module 214 may be configured to calibrate the sensor data, and the data storage memory 220 may store the calibrated sensor data points as transformed sensor data. Moreover, the processor module 214 may be configured, in some example implementations, to wirelessly receive calibration information from a display device, such as devices 14, 16, 18, and/or 20, to enable calibration of the sensor data from sensor 12. Furthermore, the processor module 214 may be configured to perform additional algorithmic processing on the sensor data (e.g., calibrated and/or filtered data and/or other sensor information), and the data storage memory 220 may be configured to store the transformed sensor data and/or sensor diagnostic information associated with the algorithms.

In some example implementations, the sensor electronics 12 may comprise an application-specific integrated circuit (ASIC) 205 coupled to a user interface 222. The ASIC 205 may further include a potentiostat 210, a telemetry module 232 for transmitting data from the sensor electronics 12 to one or more devices, such devices 14, 16, 18, and/or 20, and/or other components for signal processing and data storage (e.g., processor module 214 and data storage memory 220). Although FIG. 2 depicts ASIC 205, other types of circuitry may be used as well, including field programmable gate arrays (FPGA), one or more microprocessors configured to provide some (if not all of) the processing performed by the sensor electronics 12, analog circuitry, digital circuitry, or a combination thereof.

In the example depicted at FIG. 2, the potentiostat 210 is coupled to a continuous analyte sensor 10, such as a glucose sensor to generate sensor data from the analyte. The potentiostat 210 may also provide via data line 212 a voltage to the continuous analyte sensor 10 to bias the sensor for measurement of a value (e.g., a current and the like) indicative of the analyte concentration in a host (also referred to as the analog portion of the sensor). The potentiostat 210 may have one or more channels depending on the number of working electrodes at the continuous analyte sensor 10.

In some example implementations, the potentiostat 210 may include a resistor that translates a current value from the sensor 10 into a voltage value, while in some example implementations, a current-to-frequency converter (not shown) may also be configured to integrate continuously a measured current value from the sensor 10 using, for example, a charge-counting device. In some example implementations, an analog-to-digital converter (not shown) may digitize the analog signal from the sensor 10 into so-called "counts" to allow processing by the processor module 214. The resulting counts may be directly related to the current measured by the potentiostat 210, which may be directly related to an analyte level, such as a glucose level, in the host.

The telemetry module 232 may be operably connected to processor module 214 and may provide the hardware, firmware, and/or software that enable wireless communication between the sensor electronics 12 and one or more other devices, such as display devices, processors, network access devices, and the like. A variety of wireless radio technologies that can be implemented in the telemetry module 232 include Bluetooth, Bluetooth Low-Energy, ANT, ANT+, ZigBee, IEEE 802.11, IEEE 802.16, cellular radio access technologies, radio frequency (RF), infrared (IR), paging network communication, magnetic induction, satellite data communication, spread spectrum communication, frequency hopping communication, near field communications, and/or the like. In some example implementations, the telemetry module 232 comprises a Bluetooth chip, although the Bluetooth technology may also be implemented in a combination of the telemetry module 232 and the processor module 214.

The processor module 214 may control the processing performed by the sensor electronics 12. For example, the processor module 214 may be configured to process data (e.g., counts), from the sensor, filter the data, calibrate the data, perform fail-safe checking, and/or the like.

In some example implementations, the processor module 214 may comprise a digital filter, such as for example an infinite impulse response (BR) or a finite impulse response (FIR) filter. This digital filter may smooth a raw data stream received from sensor 10. Generally, digital filters are programmed to filter data sampled at a predetermined time interval (also referred to as a sample rate). In some example implementations, such as when the potentiostat 210 is configured to measure the analyte (e.g., glucose and/or the like) at discrete time intervals, these time intervals determine the sampling rate of the digital filter. In some example implementations, the potentiostat 210 may be configured to measure continuously the analyte, for example, using a current-to-frequency converter. In these current-to-frequency converter implementations, the processor module 214 may be programmed to request, at predetermined time intervals (acquisition time), digital values from the integrator of the current-to-frequency converter. These digital values obtained by the processor module 214 from the integrator may be averaged over the acquisition time due to the continuity of the current measurement. As such, the acquisition time may be determined by the sampling rate of the digital filter.

The processor module 214 may further include a data generator (not shown) configured to generate data packages for transmission to devices, such as the display devices 14, 16, 18, and/or 20. Furthermore, the processor module 214 may generate data packets for transmission to these outside sources via telemetry module 232. In some example implementations, the data packages may, as noted, be customizable for each display device, and/or may include any available data, such as a time stamp, displayable sensor information, transformed sensor data, an identifier code for the sensor and/or sensor electronics 12, raw data, filtered data, calibrated data, rate of change information, trend information, error detection or correction, and/or the like.

The processor module 214 may also include a program memory 216 and other memory 218. The processor module 214 may be coupled to a communications interface, such as a communication port 238, and a source of power, such as a battery 234. Moreover, the battery 234 may be further coupled to a battery charger and/or regulator 236 to provide power to sensor electronics 12 and/or charge the battery 234.

The program memory 216 may be implemented as a semi-static memory for storing data, such as an identifier for a coupled sensor 10 (e.g., a sensor identifier (ID)) and for storing code (also referred to as program code) to configure the ASIC 205 to perform one or more of the operations/functions described herein. For example, the program code may configure processor module 214 to process data streams or counts, filter, calibrate, perform fail-safe checking, and the like.

The memory 218 may also be used to store information. For example, the processor module 214 including memory 218 may be used as the system's cache memory, where temporary storage is provided for recent sensor data received from the sensor. In some example implementations, the memory may comprise memory storage components, such as read-only memory (ROM), random-access memory (RAM), dynamic-RAM, static-RAM, non-static RAM, easily erasable programmable read only memory (EEPROM), rewritable ROMs, flash memory, and the like.

The data storage memory 220 may be coupled to the processor module 214 and may be configured to store a variety of sensor information. In some example implementations, the data storage memory 220 stores one or more days of continuous analyte sensor data. For example, the data storage memory may store 1, 2, 3, 4, 5, 6, 7, 8, 9, 10, 11, 12, 13, 14, 15, 20, and/or 30 (or more days) of continuous analyte sensor data received from sensor 10. The stored sensor information may include one or more of the following: a time stamp, raw sensor data (one or more raw analyte concentration values), calibrated data, filtered data, transformed sensor data, and/or any other displayable sensor information, calibration information (e.g., reference BG values and/or prior calibration information), sensor diagnostic information, and the like.

The user interface 222 may include a variety of interfaces, such as one or more buttons 224, a liquid crystal display (LCD) 226, a vibrator 228, an audio transducer (e.g., speaker) 230, a backlight (not shown), and/or the like. The components that comprise the user interface 222 may provide controls to interact with the user (e.g., the host). One or more buttons 224 may allow, for example, toggle, menu selection, option selection, status selection, yes/no response to on-screen questions, a "turn off" function (e.g., for an alarm), an "acknowledged" function (e.g., for an alarm), a reset, and/or the like. The LCD 226 may provide the user with, for example, visual data output. The audio transducer 230 (e.g., speaker) may provide audible signals in response to triggering of certain alerts, such as present and/or predicted hyperglycemic and hypoglycemic conditions. In some example implementations, audible signals may be differentiated by tone, volume, duty cycle, pattern, duration, and/or the like. In some example implementations, the audible signal may be configured to be silenced (e.g., acknowledged or turned off) by pressing one or more buttons 224 on the sensor electronics 12 and/or by signaling the sensor electronics 12 using a button or selection on a display device (e.g., key fob, cell phone, and/or the like).

Although audio and vibratory alarms are described with respect to FIG. 2, other alarming mechanisms may be used as well. For example, in some example implementations, a tactile alarm is provided including a poking mechanism configured to "poke" or physically contact the patient in response to one or more alarm conditions.

The battery 234 may be operatively connected to the processor module 214 (and possibly other components of the sensor electronics 12) and provide the necessary power for the sensor electronics 12. In some example implementations, the battery is a Lithium Manganese Dioxide battery, however any appropriately sized and powered battery can be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some example implementations, the battery is rechargeable. In some example implementations, a plurality of batteries can be used to power the system. In yet other implementations, the receiver can be transcutaneously powered via an inductive coupling, for example.

A battery charger and/or regulator 236 may be configured to receive energy from an internal and/or external charger. In some example implementations, a battery regulator (or balancer) 236 regulates the recharging process by bleeding off excess charge current to allow all cells or batteries in the sensor electronics 12 to be fully charged without overcharging other cells or batteries. In some example implementations, the battery 234 (or batteries) is configured to be charged via an inductive and/or wireless charging pad, although any other charging and/or power mechanism may be used as well.

One or more communication ports 238, also referred to as external connector(s), may be provided to allow communication with other devices, for example a PC communication (com) port can be provided to enable communication with systems that are separate from, or integral with, the sensor electronics 12. The communication port, for example, may comprise a serial (e.g., universal serial bus or "USB") communication port, and allow for communicating with another computer system (e.g., PC, personal digital assistant or "PDA," server, or the like). In some example implementations, the sensor electronics 12 is able to transmit historical data to a PC or other computing device (e.g., an analyte processor as disclosed herein) for retrospective analysis by a patient and/or physician.

In some continuous analyte sensor systems, an on-skin portion of the sensor electronics may be simplified to minimize complexity and/or size of on-skin electronics, for example, providing only raw, calibrated, and/or filtered data to a display device configured to run calibration and other algorithms required for displaying the sensor data. However, the sensor electronics 12 (e.g., via processor module 214) may be implemented to execute prospective algorithms used to generate transformed sensor data and/or displayable sensor information, including, for example, algorithms that: evaluate a clinical acceptability of reference and/or sensor data, evaluate calibration data for best calibration based on inclusion criteria, evaluate a quality of the calibration, compare estimated analyte values with time corresponding measured analyte values, analyze a variation of estimated analyte values, evaluate a stability of the sensor and/or sensor data, detect signal artifacts (noise), replace signal artifacts, determine a rate of change and/or trend of the sensor data, perform dynamic and intelligent analyte value estimation, perform diagnostics on the sensor and/or sensor data, set modes of operation, evaluate the data for aberrancies, and/or the like.

Although separate data storage and program memories are shown in FIG. 2, a variety of configurations may be used as well. For example, one or more memories may be used to provide storage space to support data processing and storage requirements at sensor electronics 12.

Calibration

While some continuous glucose sensors rely on (and assume an accuracy of) BG values and/or factory derived information for calibration, the disclosed embodiments exploit real-time information (e.g., sensor data) to determine relative influences or certainties associated with certain calibration information and calibrate based thereon.

Figure 3:
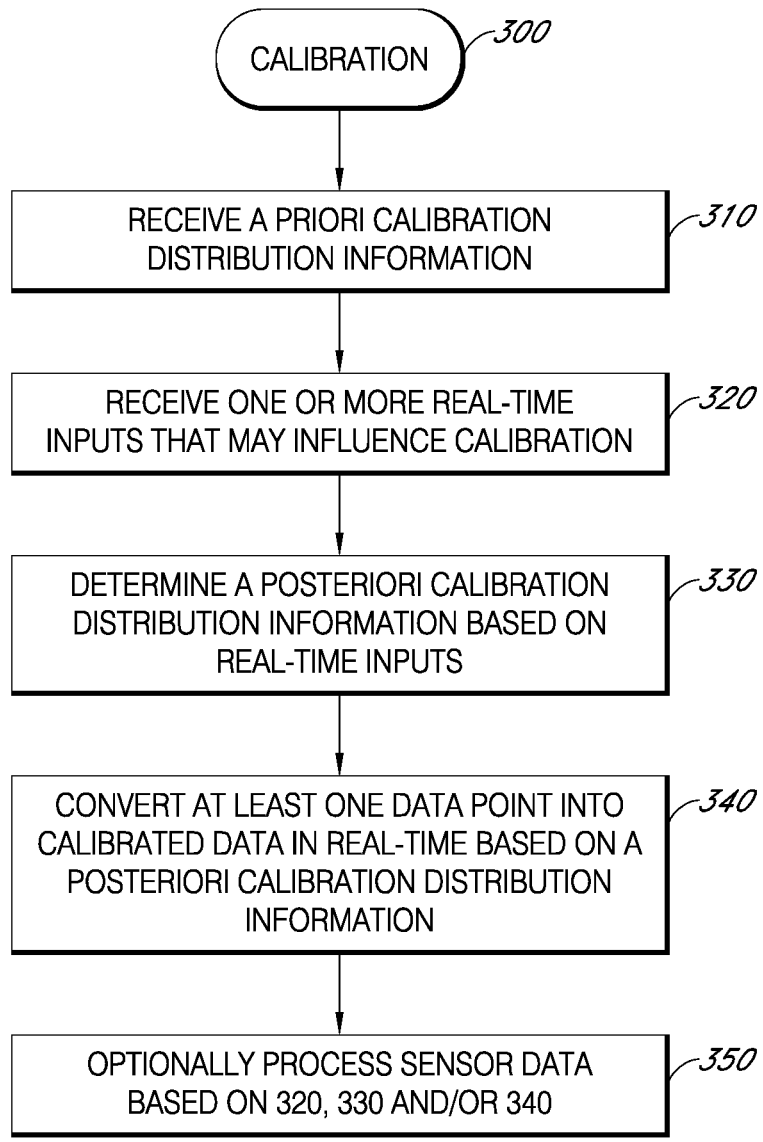
FIG. 3 is a flowchart illustrating calibration of an analyte sensor in accordance with an embodiment of the disclosure.

FIG. 3 is a flowchart 300 illustrating calibration of an analyte sensor using a priori calibration distribution information and one or more real-time inputs in accordance with an embodiment of the disclosure. At block 310, processor module 214 may be configured to receive one or more a priori calibration distributions. A priori calibration distribution information can be received from one or more different sources. For example, in some embodiments, a priori calibration distribution information can be received as information from a previous calibration and/or sensor session (e.g., same sensor system internally stored), stored in memory, coded at the factory (e.g., as part of factory settings), on a bar code of packaging, sent from the cloud or a network of remote servers, coded by a care provider, received from another sensor system or electronic device, based on results from laboratory testing, and/or the like.

As used herein, a priori information includes information obtained prior to a particular calibration. For example, from previous calibrations of a particular sensor session (e.g., feedback from a previous calibration(s)), information obtained prior to sensor insertion (e.g., factory information from in vitro testing or data obtained from previously implanted analyte concentration sensors, such as sensors of the same manufacturing lot of the sensor being and/or sensors from one or more different lots), prior in vivo testing of a similar sensor on the same host, and/or prior in vivo testing of similar sensors or different hosts. Calibration information includes information useful in calibrating a continuous glucose sensor, such as, but not limited to: sensitivity (m), change in sensitivity (dm/dt), which may also be referred to drift in sensitivity), rate of change of sensitivity (ddm/ddt), baseline/intercept (b), change in baseline (db/dt), rate of change of baseline (ddb/ddt), baseline and/or sensitivity profiles (i.e., change over a time period) associated with the sensor; linearity, response time, relationships between properties of the sensor (e.g., relationships between sensitivity and baseline, or relationships between particular stimulus signal output (e.g., output indicative of an impedance, capacitance or other electrical or chemical property of the sensor) and sensor sensitivity or temperature (e.g., determined from prior in vivo and/or ex vivo studies) such as described in U.S. Patent Publication 2012-0265035-A1, which is incorporated herein by reference in its entirety; sensor data obtained from previously implanted analyte concentration sensors; calibration code(s) associated with a sensor being calibrated; patient specific relationships between sensor and sensitivity, baseline, drift, impedance, impedance/temperature relationship (e.g., determined from prior studies of the patient or other patients having common characteristics with the patient), site of sensor implantation (abdomen, arm, etc.) specific relationships (different sites may have different vascular density). Distribution information includes ranges, distribution functions, distribution parameters (mean, standard deviation, skewness, etc.), generalized functions, statistical distributions, profiles, or the like that represent a plurality of possible values for calibration information. Taken together, a priori calibration distribution information includes range(s) or distribution(s) of values (e.g., describing their associated probabilities, probability density functions, likelihoods, or frequency of occurrence) provided prior to a particular calibration process useful for calibration of the sensor (e.g., sensor data).

For example, in some embodiments, a priori calibration distribution information includes probability distributions for sensitivity (m) or sensitivity-related information and baseline (b) or baseline-related information based on e.g., sensor type. As described above, the prior distribution of sensitivity and/or baseline may be factory-derived (e.g., from in vitro or in vivo testing of representative sensors) or derived from previous calibrations. Examples of such prior distributions of m and b can be found in FIG. 4 and FIG. 5. Although FIG. 4 and FIG. 5 exemplify Gaussian distributions, statistical, normal, log normal, empirically derived, non-parametric and/or the like may be used. While in some embodiments, Gaussian distributions best describe probabilities to continuous random variables. Some embodiments best describe probabilities with other probability distributions, including but not limited to, Pareto, Johnson, log-normal, Gompertz, uniform, beta, gamma, and discrete distributions.

Figure 5:
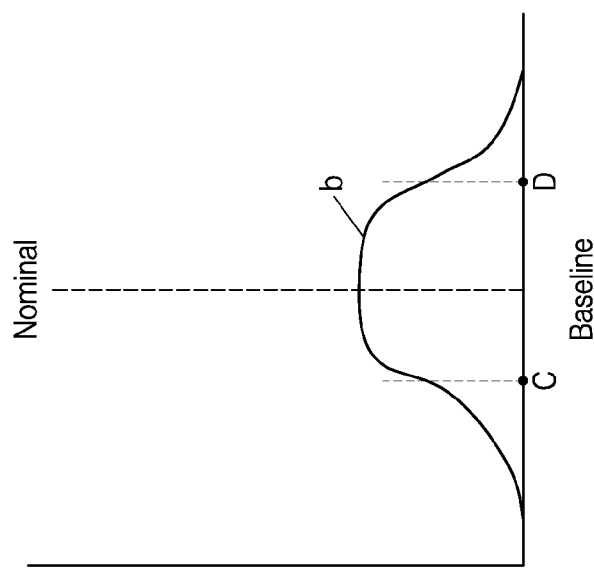
FIG. 5 is a graph that illustrates an example probability distribution for baseline in accordance with an embodiment of the disclosure.
Figure 4:
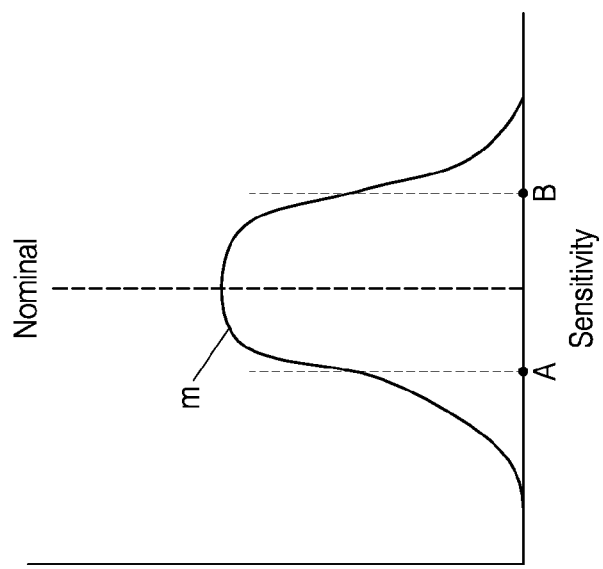
FIG. 4 is a graph that illustrates an example probability distribution for sensitivity in accordance with an embodiment of the disclosure.

FIG. 4 illustrates an example probability distribution for sensitivity in accordance with an embodiment of the disclosure. FIG. 5 illustrates an example probability distribution for baseline in accordance with an embodiment of the disclosure. It should be appreciated that as used herein, distribution information includes ranges, distribution functions, and the like. For example, in describing a range(s), the graphs in FIG. 4 and FIG. 5 may be generalized as, "sensor sensitivity most often falls between points A and B, and baseline most often falls between points C and D." However, in describing a distribution function, the graphs in FIG. 4 and FIG. 5 may be generalized as, "Sensor sensitivity falls on the sensitivity distribution curve, and Baseline falls on the baseline distribution curve." While not specifically shown, in some embodiments, properties known with high certainty, e.g., "tight distributions", may be given a greater weight than other properties, as described elsewhere herein.

Figure 6:
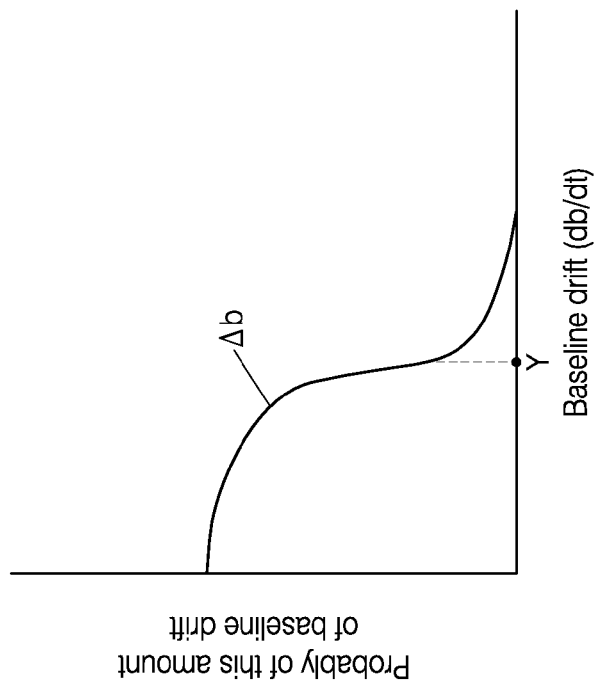
FIG. 6 is a graph that illustrates an example probability distribution for sensitivity drift in accordance with an embodiment of the disclosure.
Figure 7:
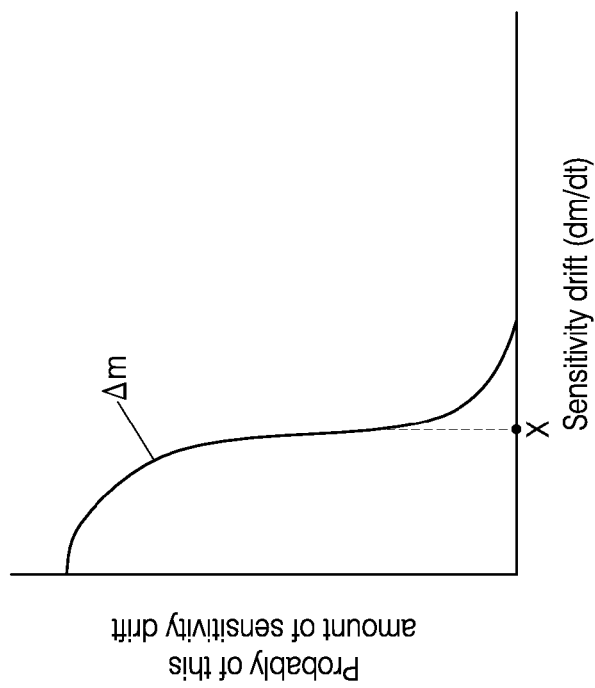
FIG. 7 is a graph illustrates an example probability distribution for baseline drift in accordance with an embodiment of the disclosure.

In some embodiments, a priori calibration distribution information includes known ranges of sensitivity and/or baseline drift (rate of change). FIG. 6 illustrates an example probability distribution for sensitivity drift in accordance with an embodiment of the disclosure. FIG. 7 illustrates an example probability distribution for baseline drift in accordance with an embodiment of the disclosure. In some embodiments, ranges may be described as, for example, "sensitivity drift is usually less than X per hour, and baseline drift is usually less than Y per hour." However, in describing a distribution function, the graphs in FIG. 6 and FIG. 7 may be generalized as, "sensor drift falls on the $\Delta m$ distribution curve, and baseline drift falls on the $\Delta b$ distribution curve."

It should also be understood that baseline and/or sensitivity value ranges and drift ranges may be patient and/or sensor specific, that is, they may depend on a priori patient and/or sensor lot information. Although FIGS. 4-7 represent a distribution of calibration information calculated at a particular time point, it should be understood that distributions of calibration information may depend on time since sensor insertion and/or a priori information relating to time dependent changes in sensitivity and baseline (for example, some sensors are known to drift up at the beginning of a particular session and drift back down at a different rate nearing the end of a sensor session (e.g., for 3, 5, 6, 7 or 10 day session).

Figure 8:
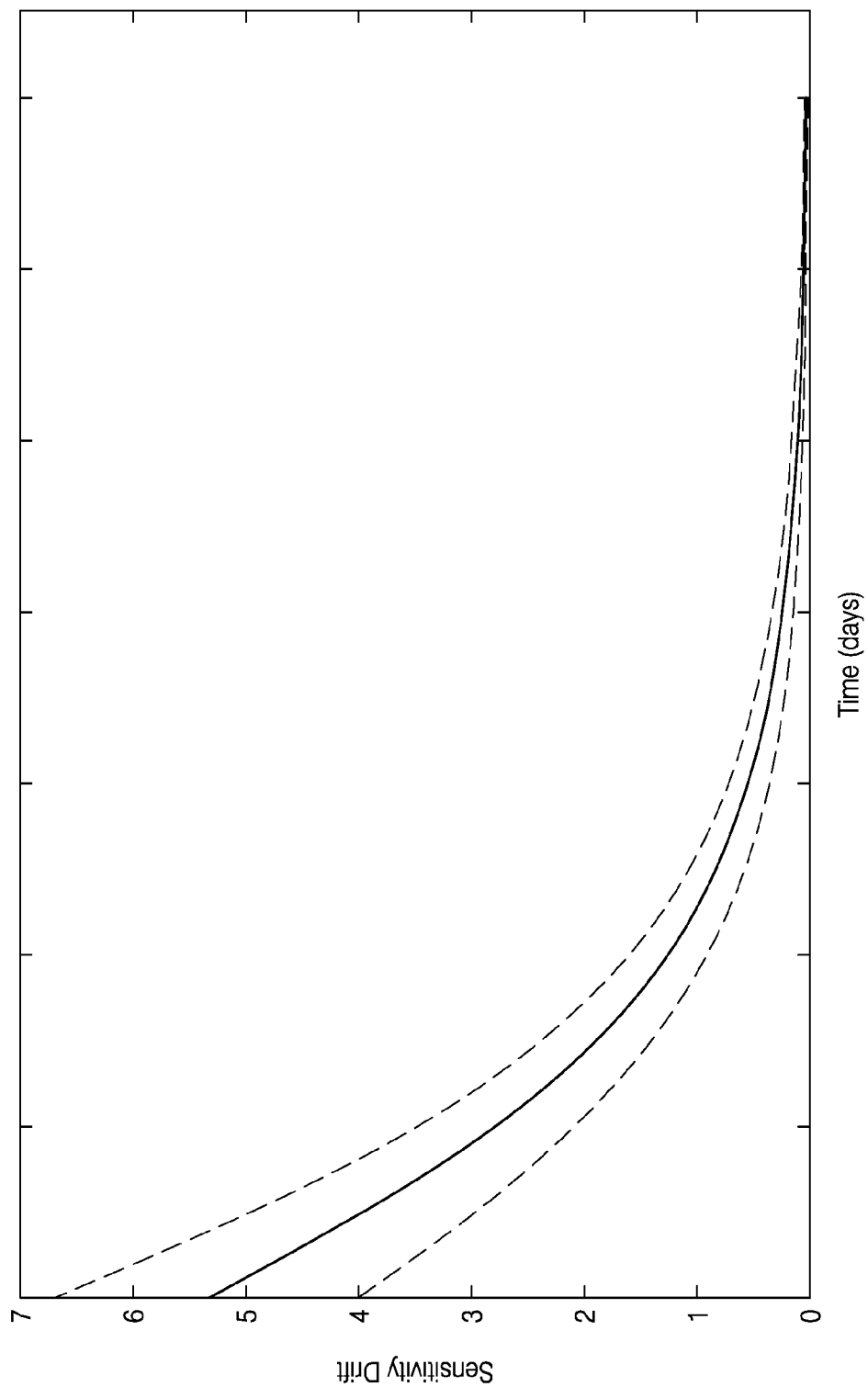
FIG. 8 is a graph that illustrates a range of drift profiles in accordance with an embodiment of the disclosure.

FIG. 8 is a graph that represents a range of possible drift profiles in one embodiment. The solid black line represents the typical sensitivity or peak sensitivity/drift profile over time, the dashed lines represents a range of possible sensitivity/drift profiles over time. In other words, because calibration information may change over time, any of the a priori calibration information described above may include not only static, but also dynamic information. For example, calibration information may be defined based on a particular sensor lot or design and/or may be defined based on time during the sensor session (post-sensor insertion). It should be noted that even when a priori distribution information has time-based profile as described above, the time-based profile may be adjusted a posteriori based on real time input. For example, if a real time input suggests that a priori calibration distribution information (e.g., a time-based sensitivity profile) is not accurate (e.g., actual drift is slower or faster than estimated), then the time-based profile should be adjusted accordingly.

While example distributions of single calibration factors have been described thus far, interdependence or correlation of multiple calibration factors exist in some sensor designs. For example, there are more or less likely/probable combinations of sensitivity and baseline for some sensor designs. Accordingly, it should be understood that a priori calibration distribution information includes relationships between multiple calibration factors, such as sensitivity and baseline. The calibration factors probabilities may also be correlated for a given calibration set, wherein the correlation is indicative of calibration parameters (such as sensitivity and baseline) are not independently estimated.

Figure 9:
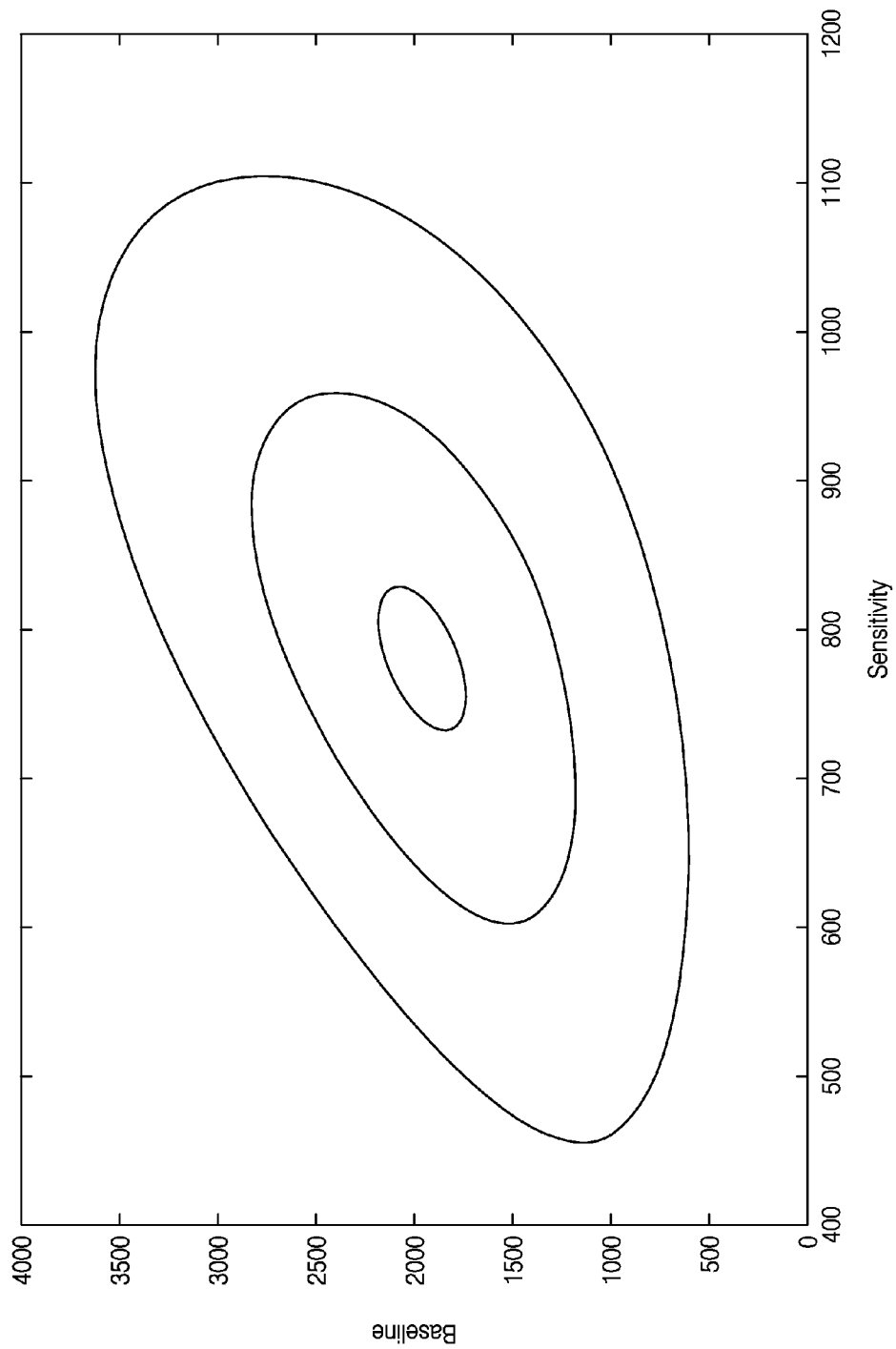
FIG. 9 is a graph that illustrates a distribution of possible correlations of sensitivity and baseline values useful in calibration of a sensor in accordance with an embodiment of the disclosure.

FIG. 9 illustrates a distribution of possible correlations of sensitivity and baseline values useful in calibration of a sensor in one embodiment. This correlation structure (probability versus sensitivity and baseline) is displayed as a contour plot. The three rings in FIG. 9 represent standard deviations of probabilities of the combinations of sensitivity and baseline, wherein the inner ring represents most probable combinations of sensitivity and baseline, and so on. To illustrate, when the sensitivity of a sensor is 500, then a baseline of 3000 is highly unlikely; when the sensitivity of a sensor is 1000, then a baseline of 3000 is more likely. In one example, wherein a plurality of possible calibration lines exist (e.g., multiple lines are within the expected error of the matched pairs or each line is based on different subsets of matched data pairs), a most probable calibration line may be selected based on probabilities described herein.

In some embodiments, a priori calibration distribution information includes range(s) of acceptable sensitivities and/or baselines (e.g., boundaries). In some embodiments, a priori calibration distribution information includes a priori guidance or validation ranges. These a priori guidance or validation ranges can be obtained from in vivo or in vitro tests (e.g., by a retrospective analysis of sensor sensitivities and/or baselines collected from a set of sensors/patients). As used herein, a priori guidance or validation ranges refer to boundaries for guiding or validating calibration factors, such as sensitivity and/or baseline, against which final calibration factors (m, b, calibration line, etc.) may be measured or compared. In some embodiments, predetermined acceptable boundaries for sensitivity and baseline may be useful for checking final calibration factors.

Figure 10:
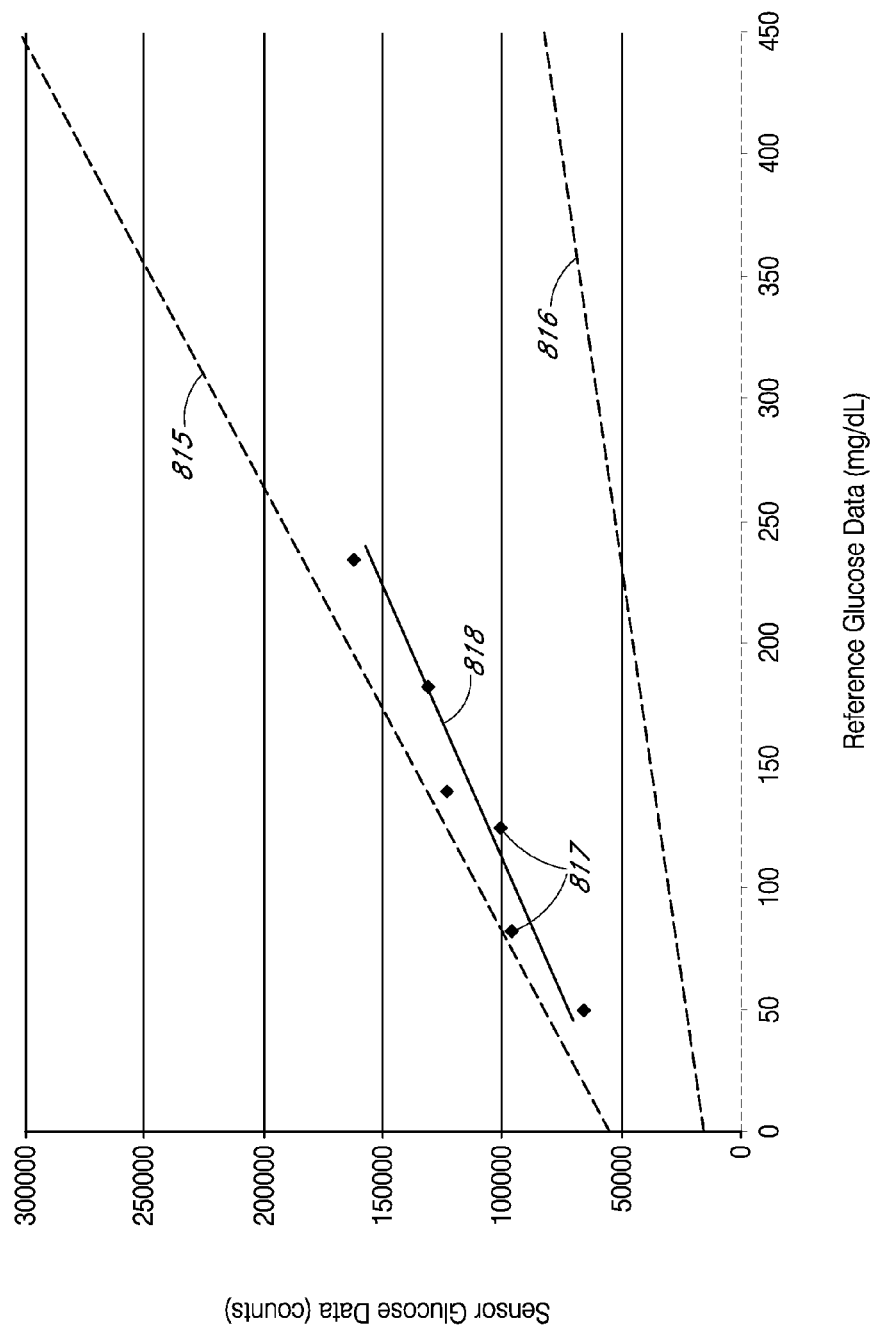
FIG. 10 is a graph that illustrates one example of using a priori information for sensitivity and baseline boundary information in accordance with an embodiment of the disclosure.

FIG. 10 is a graph that illustrates one example of using a priori information for sensitivity and baseline boundary information, in accordance with an embodiment of the disclosure. In this example, a calibration line is evaluated to determine if it falls within the predetermined acceptable boundaries. In such an example, if the calibration line does not fall within acceptable boundaries, other and/or additional steps can be taken to either correct the regression or fail-safe such that a system will not process or display errant data. This can be useful in situations wherein regression results in errant sensitivity or baseline values. For example, when points (e.g., matched pairs) used for regression do not span a sufficient range of glucose values, the resulting regression statistically may be less accurate than when the values are spread farther apart. As another example, a sensor that is not properly deployed or is damaged during deployment can yield a skewed or errant baseline signal.

Figure 11:
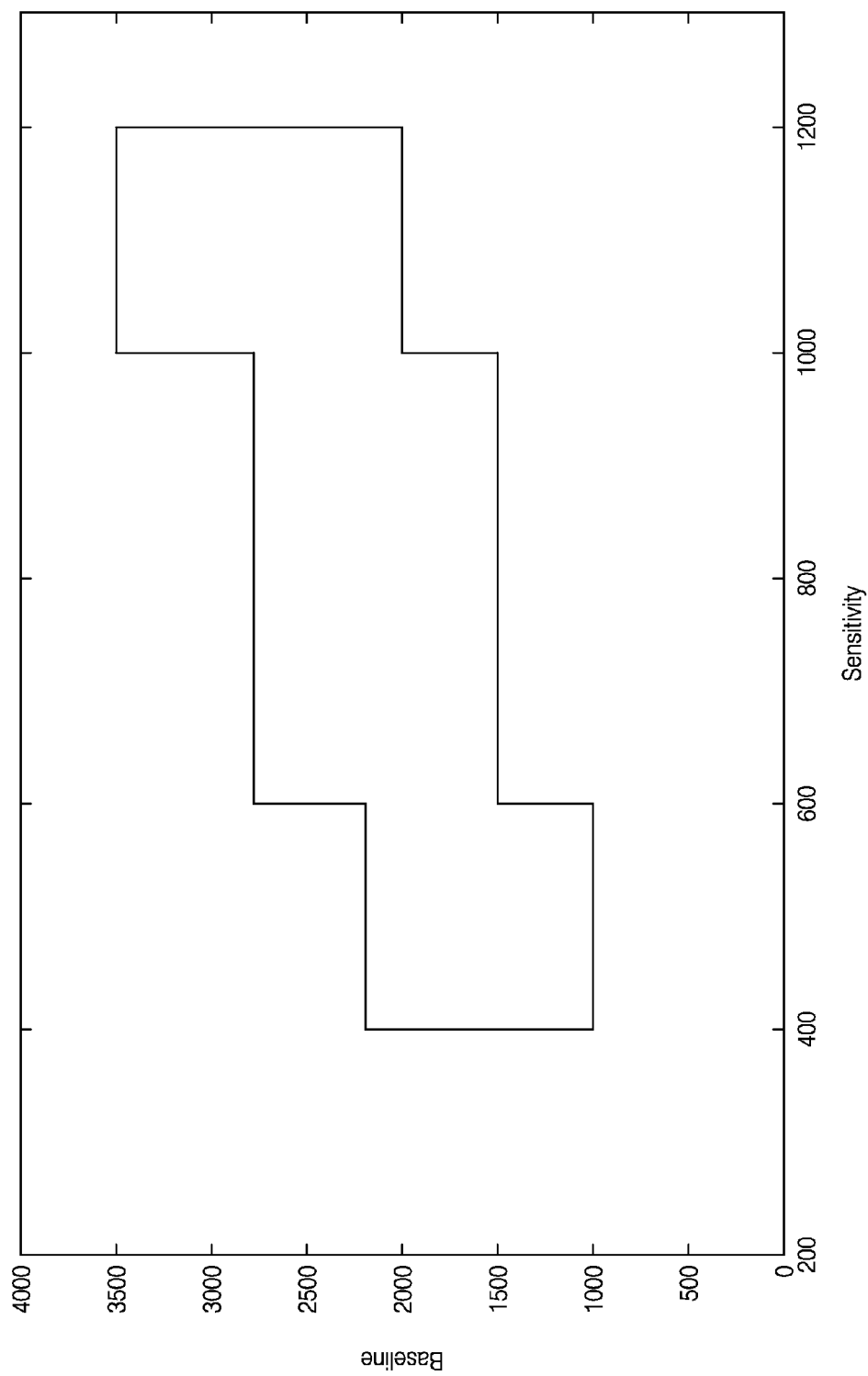
FIG. 11 is a graph that illustrates one example of using a priori information for sensitivity and baseline boundaries in accordance with an embodiment of the disclosure.

FIG. 11 is a graph that illustrates an example of using a priori information for sensitivity and baseline boundaries in one embodiment. The x-axis represents sensitivity values (e.g., in pA/mg/dL) and the y-axis represents baseline values (e.g., in pA). Similar to FIG. 10, these are acceptability boundaries for m and b.

In some embodiments, a priori calibration distribution information includes predetermined data points (i.e., a sensor data point and a reference data point that together form a matched data pair) that may be preloaded into a calibration set. Such preloaded data points provide for a greater range of calibration information and may assist in stabilizing sensitivity and allow for an improved baseline calculation. For example, these preloaded data points may encompass a certain analyte value range (e.g., where the reference analyte value ranges from a low glucose value (e.g., 40 mg/dL) to a high glucose value (e.g., 400 mg/dL)). In some embodiments, the preloaded data pairs may be determined by the manufacturer (e.g., as part of factory settings) using any known method. For example, in some embodiments, the preloaded data points may be determined using any equation that takes into consideration a low glucose value to determine a low sensor data value and takes into account a high glucose value to determine a high sensor data value. It should be appreciated, that one or more of the preloaded data points or portions of the preloaded data points may include one or more seeded (e.g., predetermined) values.

Still referring to FIG. 3, at block 320, processor module 214 may be configured to receive one or more real-time inputs that may influence sensor calibration. As used herein, "real-time inputs" are defined as data received or determined since a previous calibration process (or during, but after sensor insertion for the first calibration process performed during a sensor session (e.g., initial calibration)) that may be useful for calibration of the continuous glucose sensor. For example, real-time inputs may include the most recently received matched data pair.

In some embodiments, some real-time inputs that may be useful for the sensor calibration include, but are not limited to: internally-derived real-time data, externally-derived real-time data, and combinations of internally- and/or externally-derived real-time data. In some embodiments, internally-derived real-time data includes information generated by the sensor system in which the implanted analyte sensor (the data of which is being calibrated) is being used. Internally-derived real-time information may include any of the following types of information: stimulus signal output of sensor (e.g., impedance), sensor data measured by the sensor indicative of an analyte concentration (e.g., real-time analyte concentration information); sensor data indicative of analyte rate-of-change (e.g. glucose change in mg/dL/minute); temperature measurements; sensor data from multi-electrode sensors; sensor data generated by redundant sensors; sensor data generated by one or more auxiliary sensors; data representative of a pressure on sensor/sensor system; data generated by an accelerometer; sensor diagnostic information (e.g. noise level and noise diagnostics) and impedance, certainty level/confidence interval from feedback of another process of flow chart 300, etc.

In some embodiments, externally-derived real-time data includes information generated from sources external to the sensor, while the implanted analyte sensor (the data of which is being calibrated) is being used (during a sensor session). Externally-derived calibration information can include: glucose concentration information obtained from a reference monitor/sensor and may include type/brand of reference meter; information related to meal, insulin dosing time and amounts (e.g. manually entered or from an insulin pump), insulin estimates (e.g. "insulin on board" estimates from an insulin pump algorithm) exercise (manually entered or estimated from heart rate monitoring or accelerometer data), sleep, illness, stress, hydration, hormonal conditions, or the like. In some embodiments, externally-derived real-time data includes data derived from a source outside the continuous analyte sensor presently undergoing the calibration process, including from overlapping sensor sessions of another continuous analyte sensor on a (same) host or any sensor other than the continuous analyte sensor undergoing the calibration process, In some embodiments, externally-derived real-time data includes real-time analyte concentration information such as a blood glucose value obtained from a finger stick. However, the reference data may be based on sensor data from another substantially continuous analyte sensor, e.g., an analyte sensor described herein, or another type of suitable analyte sensor. In general, reference data (e.g., one or more reference analyte data points) may be matched with substantially time corresponding sensor data (e.g., one or more sensor data points) to provide one or more matched data pairs. In one embodiment, one reference data point is matched to one time-corresponding sensor data point to form a matched data pair. In another embodiment, a plurality of reference data points are combined (e.g., equally or non-equally weighted average, mean-value, median, or the like) and matched to one time corresponding sensor data point to form a matched data pair. In some embodiments, one or more matched data pairs may be used as part of a calibration set.

In some embodiments, combinations of internally- or externally-derived data includes: information gathered from population based data; glucose concentration of the host; error at calibration or error in matched data pair; site of sensor implantation specific relationships; time since sensor manufacture; and exposure of sensor to temperature, humidity, external factors, on shelf, and a measure of noise in an analyte concentration signal, a confidence level/level of certainty (e.g., as explained in further detail with reference to block 350), etc.

Additionally, in some embodiments, a combination of internally-derived and externally-derived data includes a trended error at calibration for sensitivity. Further detail on trended error at calibration for sensitivity may be found in U.S. patent application Ser. No. 13/796,185 entitled "Systems and Methods for Processing Analyte Sensor Data", and filed on Mar. 12, 2013, incorporated herein by reference. In some embodiments, a combination of internally-derived and externally-derived data includes end of life information for a sensor (e.g., from an end of life detection module). Further detail on sensor end of life may be found in U.S. patent application Ser. No. 13/733,742, entitled "End of Life Detection for Analyte Sensors", and filed on Jan. 3, 2013, incorporated herein by reference. In some embodiments, a combination of internally-derived and externally-derived data includes outlier detection information (e.g., from an outlier detection module). Further detail on outlier detection information may be found in U.S. patent application Ser. No. 13/733,810, entitled "Outlier Detection for Analyte Sensors", and filed on Jan. 3, 2013, incorporated herein by reference. In some embodiments, a combination of internally-derived and externally-derived data includes the number of days the sensor has been in use, e.g., the days since implant. Further detail related to the number of days the sensor has been in use may be found in U.S. patent application Ser. No. 13/796,185 entitled "Systems and Methods for Processing Analyte Sensor Data", and filed on Mar. 12, 2013, and/or U.S. patent application Ser. No. 13/733,742, entitled "End of Life Detection for Analyte Sensors", and filed on Jan. 3, 2013, both previously incorporated by reference. In some embodiments, a combination of internally-derived and externally-derived data includes a sensor noise information (e.g., levels and/or severities). Further detail on sensor noise information may be found in U.S. Pat. No. 8,260,393, incorporated herein by reference. In some embodiments, a combination of internally-derived and externally-derived data includes confidence or certainty information, e.g., from block 350. Further detail on confidence or certainty information will be discussed below with reference to block 350.

In some embodiments, processor module 214 may be configured to determine the real-time value of a first input. In some embodiments, the processor module 214 may check to see if the real-time value of the first input is in acceptable range. For example, whether a received reference glucose value is within a range of glucose (e.g., between 40 and 400 mg/dL). Further detail on inclusion criteria for BG values may be found in U.S. Pat. No. 7,778,680, incorporated herein by reference.

In general, error checks, such as checking to see if the input is within an acceptable range, at any step described in FIG. 3 may be used and cause feedback or feedforward to another block/step responsive thereto. For example, a flagged outlier may feed outlier information into determining the distribution associated with the BG input and/or matched data pair associated therewith, as described in greater detail below.

In some embodiments, confidence or certainty feedback determined by any one or more of blocks 310-350, and may be used as a real-time input herein, which advantageously allows calibration factor(s) and calibrated sensor data resulting therefrom to be influenced by the level of confidence or certainty to account for any error or give a more informed range or distribution of values, resulting in calibrated sensor data that is the most statistically probable result, while still accounting for errors and other influencing inputs.

Still referring to FIG. 3, at block 330, processor module 214 may be configured to form a posteriori calibration distribution information based in the one or more real-time inputs from block 320. In some embodiments, forming a posteriori calibration distribution information includes an adjustment (e.g., shifting and/or changing) of the a priori distribution information. In some embodiments, forming a posteriori calibration distribution information includes creation of new range or distribution information based on the real-time input(s).

In some embodiments, processor module 214 may be configured to adjust the a priori calibration distribution information by loosening or tightening an a priori distribution of possible sensitivities based on the real time input, thereby forming an a posteriori distribution of possible sensitivities. It should be understood that real time inputs and resulting a posteriori distributions, such as described in more detail elsewhere here, may be applicable to any of the a priori calibration distributions, whereby tighter distributions may be obtained a posteriori, after which the a posteriori calibration distribution information may become a priori calibration distribution information at the next calibration of the sensor session (or another sensor session). Conversely, some real-time inputs will result in broader calibration distributions a posteriori, for example when if the inputs indicate sensor fault conditions or physiological conditions that sensor state estimation less reliable.

Figure 12:
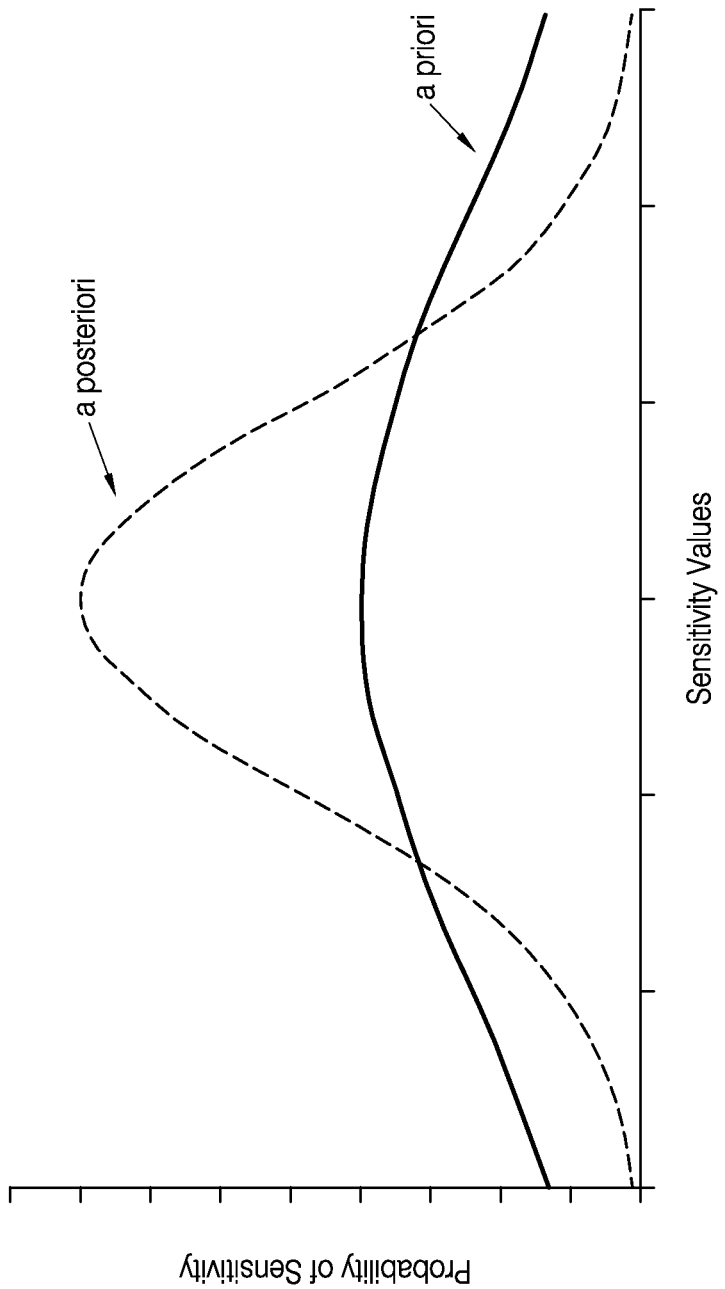
FIG. 12 is a graph that illustrates an example sensitivity distribution curve that has been adjusted in accordance with an embodiment of the disclosure.

In one example illustrated in FIG. 12, a priori calibration distribution information is tightened, a posteriori, based on a high BG input (e.g., greater than about 120 mg/dL), because high BG values generally provide more sensitivity information than lower BG values. FIG. 12 illustrates an example sensitivity distribution curve that has been adjusted in accordance with an embodiment of the disclosure. In FIG. 12, the a priori distribution of sensitivity (m) is shown as a solid line and the a posteriori distribution of m is shown as a dashed line. Additionally or alternatively, the center of the distribution may be shifted based on the real time input(s). Although this simple examples illustrates changing a single distribution (sensitivity) based on a single real-time input (BG value), it should be appreciated by one skilled in the art that any number of distributions may be changed based on any number of real time inputs, and that the distributions may shift in known ways in relation to each other. For example, a single BG value may change and/or shift sensitivity and baseline distributions and the correlations or relationship between them. Similarly, a change in a sensitivity distribution may cause a change in a baseline distribution based on known relationships between sensitivity and baseline.

Figure 13:
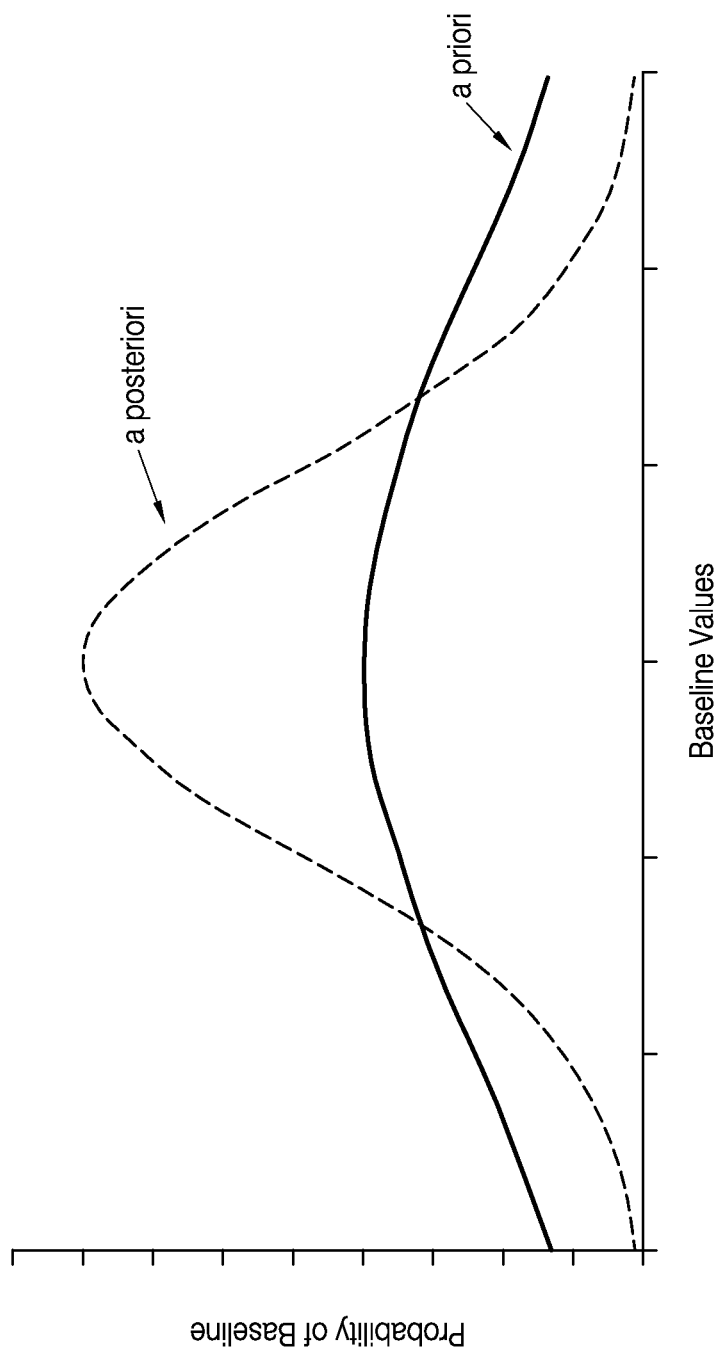
FIG. 13 is a graph that illustrates an example baseline distribution curve that has been adjusted in accordance with an embodiment of the disclosure.

In some embodiments, processor module 214 may be configured to adjust the a priori calibration distribution information by loosening or tightening an a priori distribution of possible baselines based on the real time input, thereby forming an a posteriori distribution of baselines. In one example illustrated in FIG. 13, a priori calibration distribution information is tightened based on a low BG input (e.g., less than about 120 mg/dL), because low BG values generally provide more baseline information than higher BG values. FIG. 13 illustrates an example baseline distribution curve that has been adjusted in accordance with an embodiment of the disclosure. In FIG. 13, the a priori distribution of baseline (b) is shown as a solid line and the a posteriori distribution of b is shown as a dashed line. Additionally or alternatively, the center of the distribution may be shifted based on the real time input(s). Although this simple example illustrates changing a single distribution (sensitivity) based on a single real-time input (BG value), it should be appreciated by one skilled in the art that any number of distributions may be changed based on any number of real time inputs, and that the distributions may shift in known ways in relation to each other. For example, a BG value in combination with feedback from block 350 of a previous calibration may be used to further change and/or shift sensitivity and/or baseline distributions.

Figure 14:
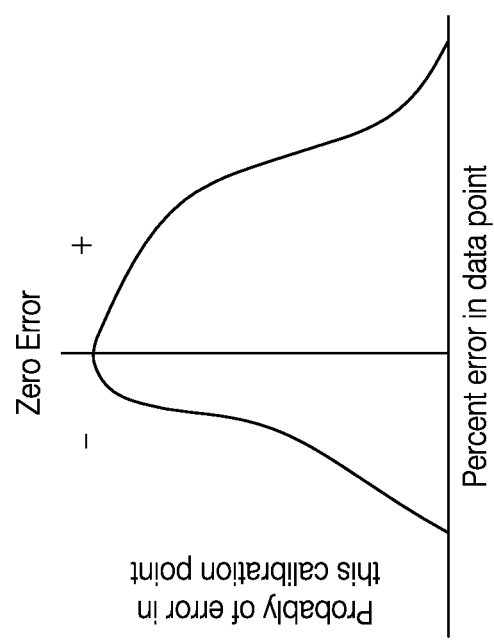
FIG. 14 is a graph that illustrates a distribution of possible BG values is created from the real-time input, a posteriori, whereby a range or distribution of possible BG values is assigned based on historical information, in accordance with an embodiment of the disclosure.

In some embodiments, processor module 214 may be configured to form a posteriori calibration distribution by creating a new range or distribution of calibration information based on the real time input. In one example illustrated in FIG. 14, a distribution of possible BG values is created from the real-time input of a glucose reference value, a posteriori, whereby a range or distribution of possible BG values is assigned based on historical information. Sources of the historical information may include, for example, the sensor itself, information obtained from cloud storage, information stored in a lookup table, etc. Alternatively, the range or distribution assigned to the real-time input may be obtained by using any number of algorithms to calculate the range. For example, in some circumstances, a probability of error in the calibration point exists. This exemplary embodiment exploits the knowledge that conventional analyte meters (e.g., self-monitored blood analyte tests) are known to have a +−20% error in analyte values. Additionally, gross errors in analyte readings are known to occur due to patient error in self-administration of the blood analyte test, or incorrect manual data entry of reference values. In one such example, if the user has traces of sugar on his/her finger while obtaining a blood sample for a glucose concentration test, then the measured glucose value will likely be much higher than the actual glucose value in the blood. Additionally, it is known that self-monitored analyte tests (e.g., test strips) are occasionally subject to manufacturing error. For ease of explanation, this distribution may be approximated as, "Sensor and BGM error/inaccuracy is usually less than ±X %" or if it is asymmetric, "Error/inaccuracy is usually between −Y % and Z %." FIG. 12 illustrates an example probability distribution for error in a calibration point in accordance with an exemplary embodiment of the disclosure. In this exemplary embodiment, the probability distribution of FIG. 12 may be applied to a real time BG value input, thereby forming a posteriori calibration distribution information from the real time BG value that includes the uncertainty associated with a self-monitored blood glucose values used for calibration In some embodiments, the a posteriori calibration distributions information is also updated based on the glucose level and glucose rate-of-change associated with the match pair. For example, the sensitivity distribution may become tighter if the reference glucose value (level) expands the range of the calibration set. As another example, the sensitivity distribution may become looser if the glucose rate-of-change associated with the reference glucose value is indicative of rapidly changing glucose levels.

In some embodiments, forming a posteriori calibration distribution includes weighting certain calibration information, for example adaptively adjusting the weighting of past or present BG inputs (matched data pairs used in the calibration set for determining sensitivity and/or baseline based on the real-time information. In some embodiments, forming a posteriori calibration distribution information includes hierarchical modeling, likelihood analyses, or the like. In an embodiment that utilizes hierarchical modeling, a priori distributions may be generated using a weighting scheme, for example that weights BG inputs based on information associated with the BG input (e.g., timing, glucose level, glucose rate-of-change and other data associated with the BG input). For example, if one were to assume that every sensor that is used to measure glucose in an individual has a sensitivity that falls within a large distribution, S0. However, based on read time inputs (e.g., information about the host/patient, timing, conditions under which BG input measurements were obtained, etc.), the sensitivity may have a much tighter distribution (S1), which is a subset of the larger distribution S0. Hierarchical modeling is a method where one starts with a family of a priori distributions and selects model parameters (e.g., age, gender, study design, etc), whereby a specific a priori distribution can be used to match the experimental conditions, a posteriori. Accordingly, likelihood functions are used to calculate a posteriori distributions from a priori distributions using a Bayesian approach, as it is well known in the art. Thus, correct a priori distributions (i.e., that are relevant to experimental conditions) result in tighter a posteriori distributions.

Figure 15:
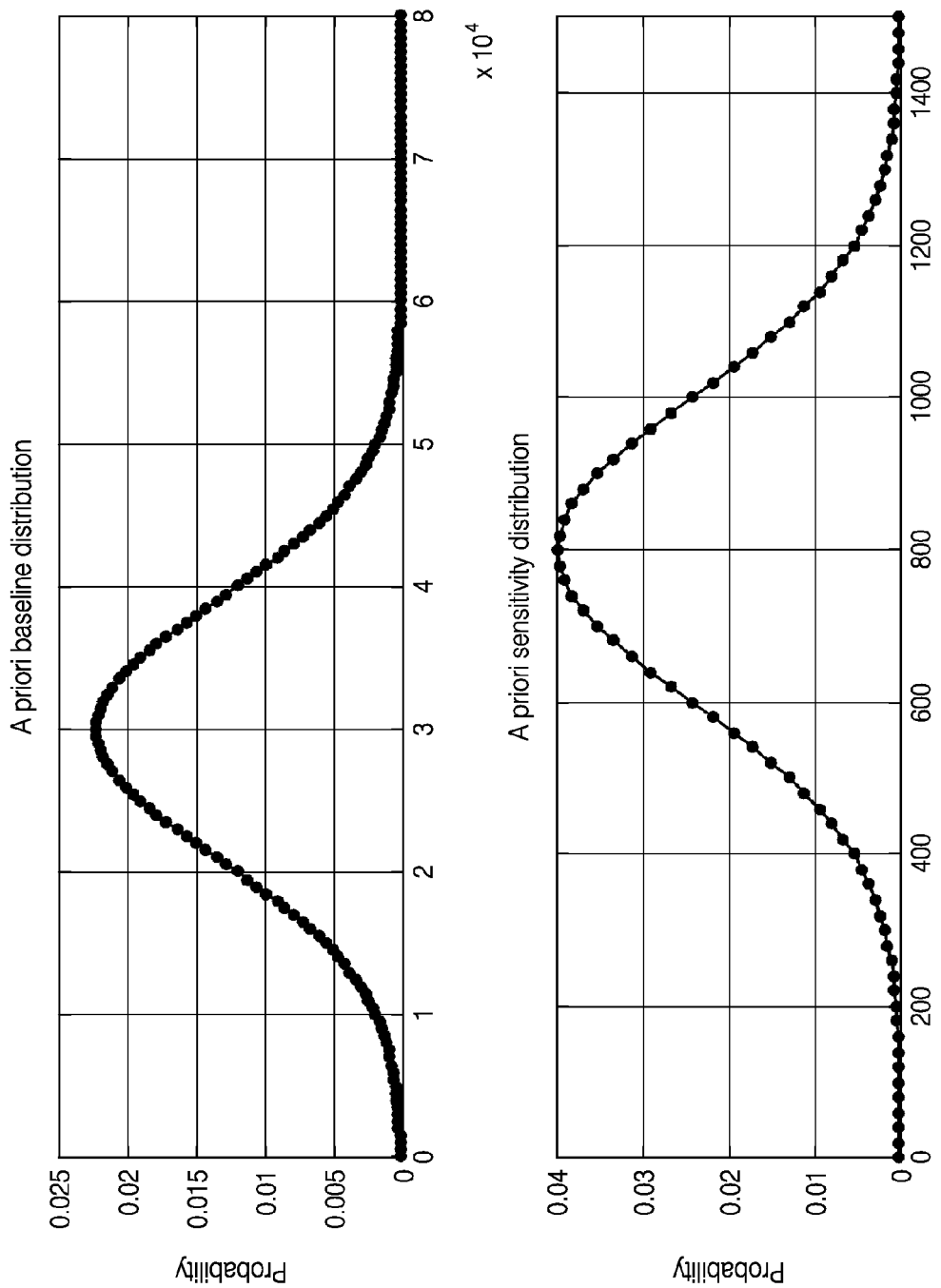
FIG. 15 illustrates Gaussian probability distributions for both baseline and sensitivity for a sensor, in accordance with an embodiment of the disclosure.
Figure 16:
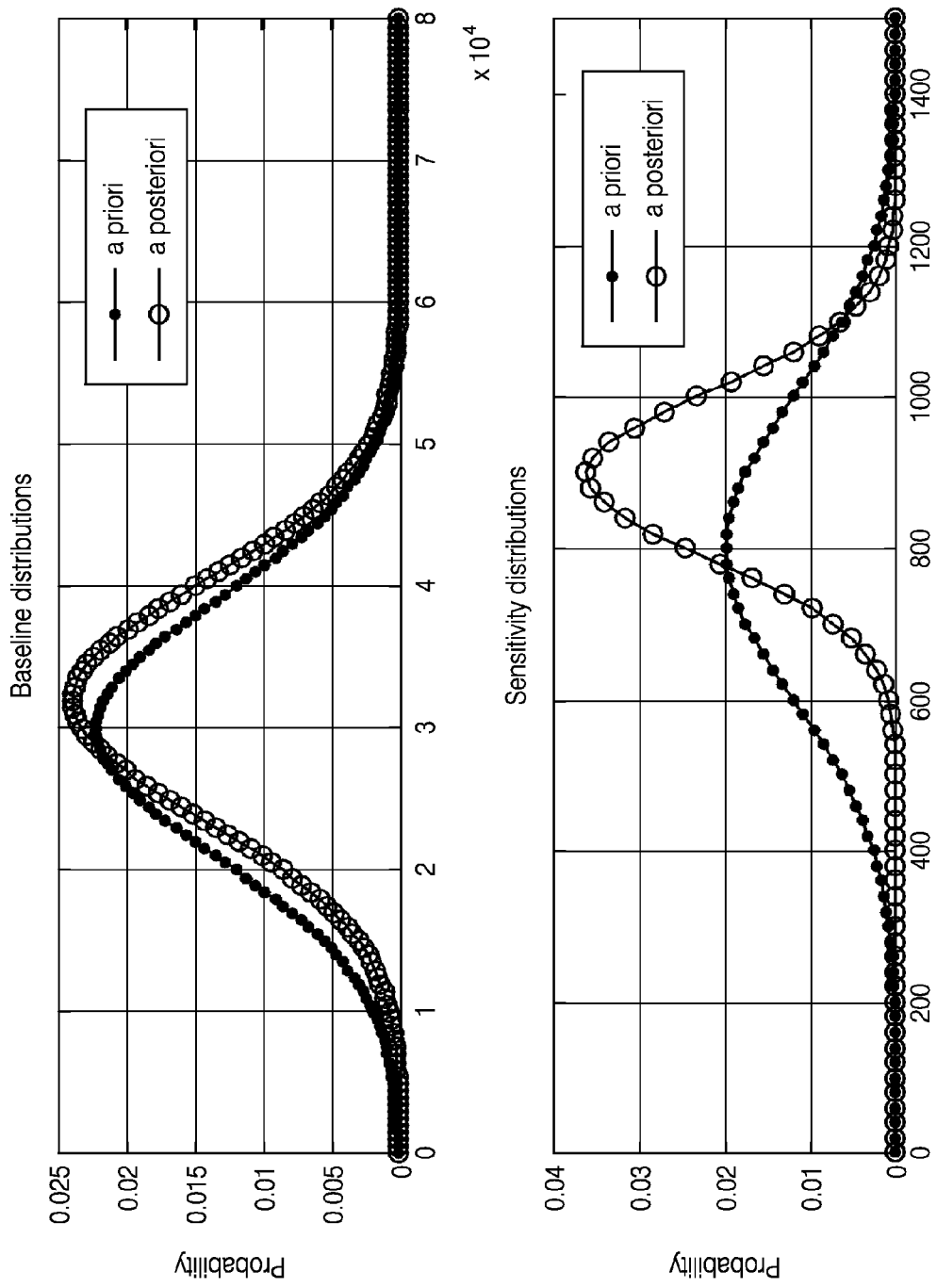
FIG. 16 is a graph that illustrates an example of a priori and a posteriori distributions of baseline and sensitivity using the Bayesian learning approach, in accordance with an embodiment of the disclosure.

FIG. 15 illustrates a priori Gaussian probability distributions for baseline and sensitivity for a sensor in one example. However, after evaluating one or more real-time inputs that may influence the calibration e.g., blood glucose and sensor output values, these distributions may be corrected using a Bayesian learning approach, resulting in a posteriori distributions (FIG. 16), for example, calculated from a priori distributions (FIG. 15) and likelihood functions using the Bayes' theorem. FIG. 16 illustrates an example of a priori and a posteriori distributions of baseline and sensitivity using the Bayesian learning approach using Likelihood function (L), which is described herein. Upon receiving and processing the real-time inputs, a likelihood of the resulting sensitivity and baseline is evaluated given the a priori distribution is calculated. Likelihood is the product probabilities of observing individual data using the prior probability distributions. For example, in FIG. 15, the likelihood of a sensitivity of 1200 is about 0.006. Similarly the Likelihood of a sensitivity of 1200 and a sensitivity of 1100, after two real-time inputs and associated calibration processing, given the distribution of FIG. 15, is the product of individual probabilities, L=0.006*0.01. Once the Likelihood is calculated, the a posteriori distribution of the sensitivity after the second real-time input and associated calibration processing is evaluated from the Bayes' theorem as: Posterior is proportional to Prior*Likelihood.

Figure 19:
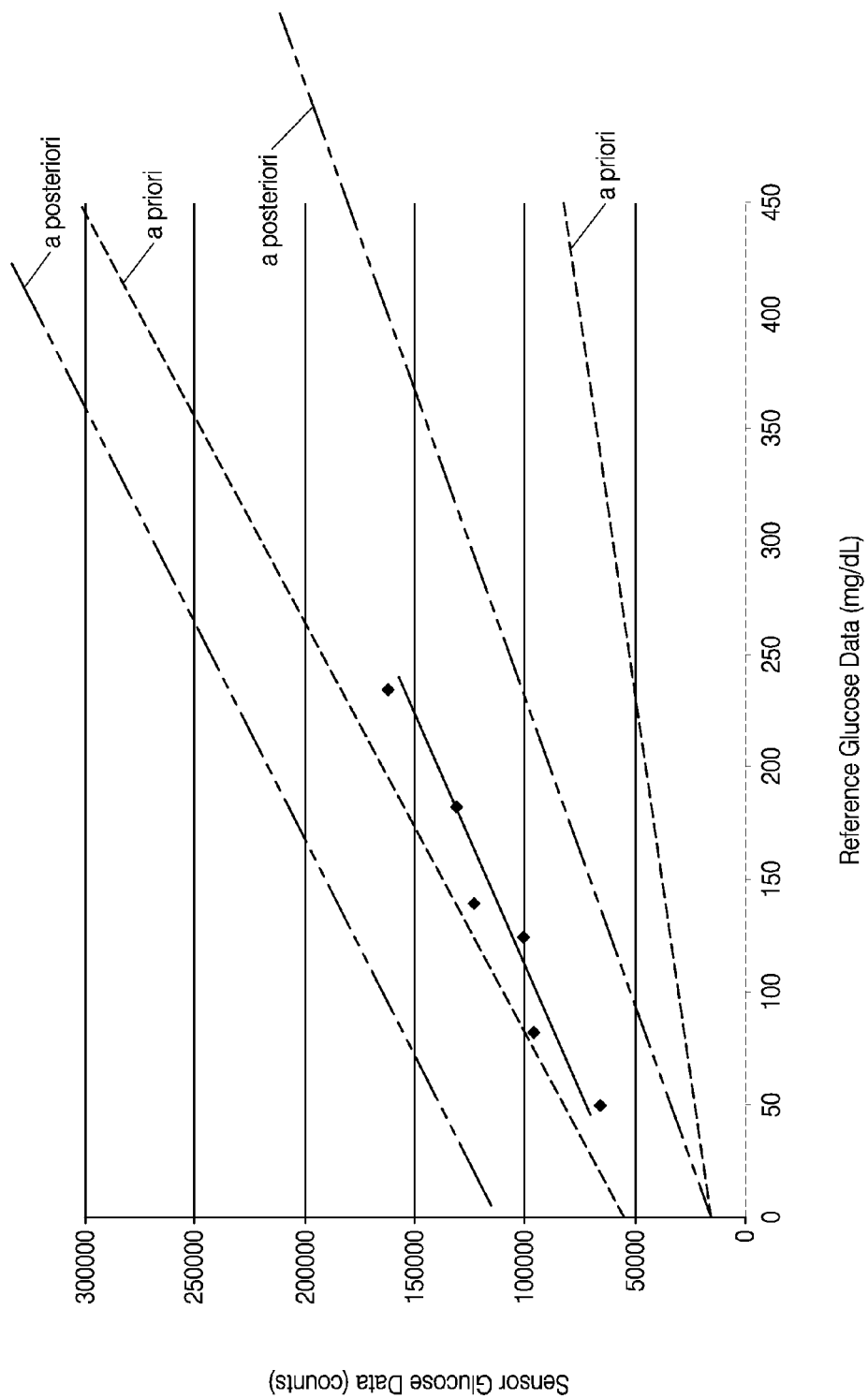
FIG. 19 is a graph that illustrates an adjustment of a posteriori boundary parameters as compared to a priori boundary parameters one example of using a priori information for sensitivity and baseline boundary information in accordance with an embodiment of the disclosure.

In some embodiments, forming a posteriori calibration distribution information includes modifying a priori guidance or validation ranges, such as those shown in FIG. 10, which provides an example of a priori calibration distribution information for sensitivity and baseline in accordance with an embodiment of the disclosure. In one example, described in more detail with reference to FIG. 19, a posteriori guidance or validation ranges may be determined based on BG input and a baseline function. In such an example, pre-implant information includes a baseline function to determine, a posteriori, baseline values, guidance and/or validation ranges based on real-time input (i.e., BG input).

Figure 17:
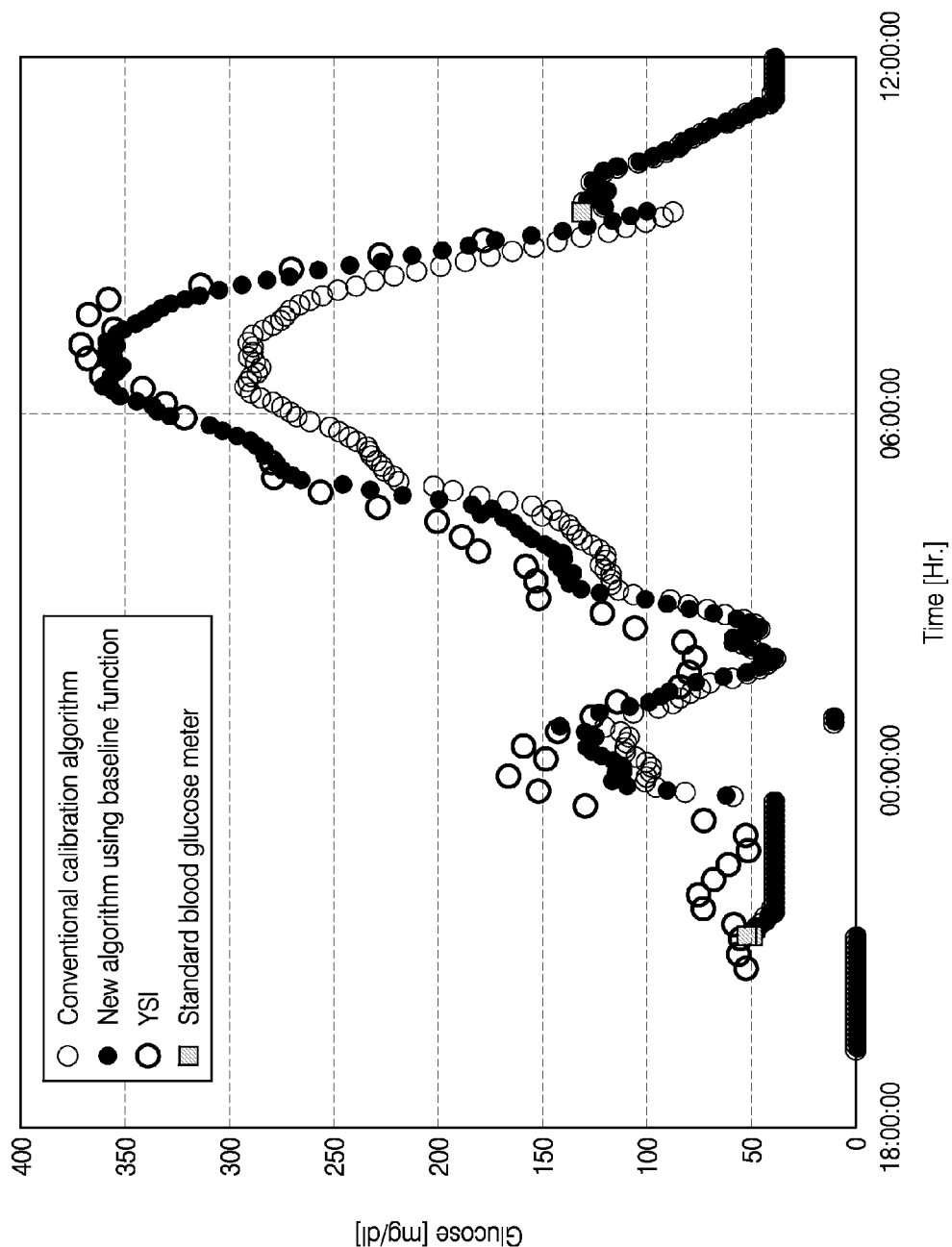
FIG. 17 is a graph that illustrates glucose data from a host overtime, including sensor data calibrated according to a disclosed embodiment compared to sensor data calibrated using a conventional algorithm, YSI measurements and standard blood glucose meter measurements.

In some embodiments, a baseline function is configured to take into account reference data (e.g., blood glucose values or BG), and estimate a baseline %. Thereafter the baseline % may be used as a multiplier with sensor data (e.g., counts) to produce a baseline value. The baseline value may also be used, in some embodiments, to update the centering of the baseline of the a priori guidance or validation range, as described in more detail elsewhere herein. Using a baseline algorithm and a BG value may result in a better calibration for example, by providing improved baseline estimation for sensor data values and validation ranges (including sensitivity and baseline), such as shown in FIG. 17, which is a graph that illustrates improved accuracy of real-time sensor data reported on the user interface. As described herein, the baseline function algorithm advantageously fits the calibration line against a moving range that is more representative of what is occurring in real-time than with a conventional algorithm. In FIG. 17, sensor data based on the baseline function algorithm described herein more closely tracks YSI (gold standard) measurements as compared to a conventional algorithm.

In some embodiments, a real-time input may include real time processed uncertainties, probabilities, confidences, or the like, such as determined at block 350 and included in a feedback loop (e.g., via 320) from previous or current calibration procedures, whereby a posteriori ranges or distributions may be determined.

At block 340, processor module 214 is configured to convert at least one sensor data point into calibrated data in real time based at least in part on the a posteriori calibration distribution information determined at block 330. In some embodiments, one or more calibration factors (e.g., sensitivity and/or baseline) are determined based at least in part on the a posteriori calibration distribution information and the selected calibration factor(s) applied in a conventional manner to the uncalibrated sensor data (e.g., using y=mx+b) to convert the at least one sensor data point as may be appreciated by one skilled in the art. In some embodiments, a plurality of possible values for each of the one or more calibration factors (e.g., sensitivity and/or baseline) may be determined based on the a posteriori calibration distribution information, to which a voting, weighting or averaging function may be applied to the plurality of possible one or more calibration factors and/or resulting calibrated sensor data derived therefrom. In some embodiments, a range of values (e.g., based on probabilities) for the one or more calibration factors (e.g., sensitivity and/or baseline) may be determined based at least in part on the a posteriori calibration distribution information, which may be used to determine a range of possible calibrated sensor data values for a given confidence interval (e.g. the glucose is between 77 an 85 mg/dL with a 99% confidence interval).

In one example, wherein a distribution of sensitivities has been determined a posteriori, the processor module is configured to convert the sensor data point (e.g., count) to a range or distribution of possible calibrated data values (e.g., glucose concentration value) using a range or distribution of possible sensitivities in the distribution (e.g., which may be cut off at a standard deviation, confidence limit, or other measure of statistical certainty). The resulting range or distribution of possible calibrated data values may be multiplied by the probability of each calibrated data value based on a weighting or voting based on the probability of its associated sensitivity. Additionally or alternatively, the resulting range or distribution of possible calibrated data values may be reported (e.g., to a control loop for an insulin pump or to alarming algorithm). Although an example of using a single calibration factor has been described, one skilled in the art should appreciate how to apply the same principles to multiple calibration factors (information) and/or relationships there between.

Although sensitivity and/or baseline are often exemplified in the description herein, the one or more calibration factors (for which calibration distribution is determined a posteriori) may be any of the factors selected from the list including, but not limited to: sensitivity (m), rate of change of sensitivity (ddm/ddt), baseline/intercept (b), rate of change of baseline (ddb/ddt), sensitivity profiles associated with the sensor; relationships between particular stimulus signal output (e.g., impedance) to sensor sensitivity; relationships between particular stimulus signal output to sensor temperature; sensor data obtained from previously implanted analyte concentration sensors; calibration code associated with a sensor being calibrated; patient specific relationships between sensor and sensitivity, and relationships between particular stimulus signal output (e.g., impedance) to temperature.

In some embodiments, the processor module 214 may use a probability analysis, fuzzy logic, decision functions, various subroutines, or the like, to determine the one or more calibration factors and/or calibrated data derived therefrom, based at least in part on the a posteriori calibration distribution information. Notably, the processor module 214 may further use the a priori calibration distribution information (310), real-time input (from 320) or other information in converting the at least one data point into calibrated data in real time (at 340).

In some embodiments, probability analyses include, but are not limited to: Bayesian Analysis, Maximum Likelihood Estimation, Generalize Linear Models, Descriptive Statistics, Computational Phylogenics, Error Analysis, Estimators, Markov Processes, Moment, Multivariate statistics, nonparametric statistics, probability, random numbers, random walks, rank statistics, regression, runs, statistical asymptotic expansions, statistical distributions, statistical indices, statistical tests, time-series analyses, or the like. Decision fusion may provide a Fused Bayesian likelihood estimate based on sensitivity and specificity of individual.

In embodiments wherein the one or more calibration factors (e.g., sensitivity and/or baseline) are determined based at least in part on the a posteriori calibration distribution information and the selected calibration factor(s) applied in a conventional manner to the uncalibrated sensor data, the one or more calibration factors may be applied to the at least one sensor data point using, e.g., a transformation function. For example, in some embodiments, a transformation function based on y=mx may be used for sensors when only sensitivity is used to convert out sensor data. However, in other embodiments, a transformation function that includes a determination of b may be used (e.g., for sensors including baseline or background), such as y=b or y=mx+b. Other compensations may also be applied to the transformation functions, for example, sensitivity drift, temperature, or other calibration factors, as may be appreciated by one skilled in the art. A further discussion of possible transformation functions may be found in U.S. patent Ser. No. 13/796,185 entitled "Systems and Methods for Processing Analyte Sensor Data", and filed on Mar. 12, 2013, incorporated by reference herein.

In some embodiments, a range of values for the one or more calibration factors may be determined based at least in part on the a posteriori calibration distribution information, which may be used to determine a range (e.g., array or vector) of possible sensor data values. In some embodiments, a plurality of possible values for each of the one or more calibration factors may be determined based on the a posteriori calibration distribution information, to which a voting, weighting or averaging function may be applied to the plurality of possible one or more calibration factors and/or resulting calibrated sensor data derived therefrom.

Figure 18:
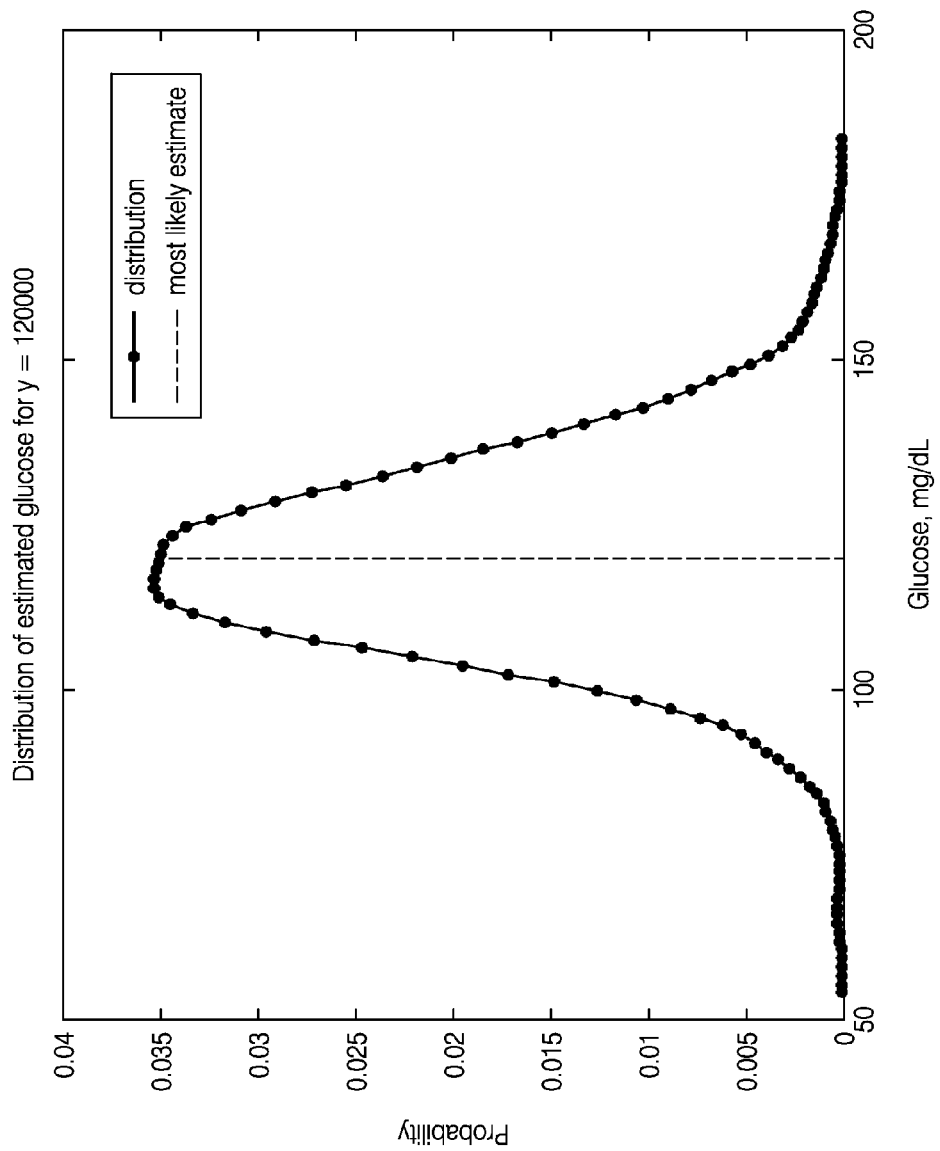
FIG. 18 a graph that shows a distribution of possible glucose values based on a distribution of sensitivity and baseline values in accordance with a disclosed embodiment.

In linear regression, the equation, Y=X*B is solved, where B is vector (distribution) of baseline (b) and sensitivity (m). Y is sensor signal counts. X is glucose in mg/dL. In contrast to conventional methods is to estimate values based on baseline and sensitivity using linear regression and calculating Y for each value of X; in a Bayesian approach, each variable may be represented by a distribution instead of a scalar value. Thus, X, Y, and B all have distributions. Thus Y can be calculated as the most likely value (scalar), or a set of values described by a distribution. Y may be calculated as a scalar by using the mean baseline and mean sensitivity, or Y can also be a distribution where all possible values of Y are generated, but some are more likely than others. FIG. 18 a graph that shows a distribution of possible glucose values based on a distribution of sensitivity and baseline values, from which a most likely glucose value can be obtained.

In some embodiments, the processor module 214 may use a particular weighting scheme that adapts based on the real-time input. For example, when a most recent BG input (and associated matched data pair) has a higher certainty associated therewith, the matched data pairs (BG input) may be weighted more heavily than other BG input associated with a lesser certainty. These certainties may also be based a priori calibration distribution information such as drift estimates (e.g., estimates of change in sensitivity over time).

In some embodiments, the calibrated sensor data may be converted based on advance calibration techniques involving automatic, self-calibration, e.g., without using reference analyte values for BG input after point of use, such as described in U.S. Patent Publication No. 2012/0265035, which is incorporated herein by reference in its entirety.

At block 350, processor module 214 is configured to further process data from blocks 310, 320, 330 and 340. In some embodiments, the processing of data from blocks 310, 320, 330 and 340 may include determining a level of certainty associated with calibration information and/or calibrated sensor data resulting therefrom. In some embodiments, the level of certainty determined for the calibrated sensor data and/or calibration from which is transformed, may be useful in acknowledging and refining trending information (e.g., such as tightening or shifting a distribution resulting in a more refined a priori or a posteriori distribution).

In some embodiments, the processing of data from blocks 310, 320, 330 and 340 may include outputting via transmission and/or display calibrated sensor data and/or a certainty associated therewith. For example, the output may be based on the level of certainty determined, for example, when a level of certainty meets certain criteria (e.g., exceeds a predetermined threshold), a transmission of the sensor data to a closed loop system may indicate the high level of certainty, and the closed loop algorithms may use the level of certainty to determine how aggressively a particular therapy may be applied (e.g., based on an assignment of algorithmic parameters). As another example, when a level of certainty meets other criteria (e.g., does not exceed a predetermined threshold), the transmission of the sensor data to a closed loop system may indicate a lower level of certainty, and the closed loop algorithm may use the level of certainty to provide certain fail-safes and/or open the closed loop (e.g., require user interaction), or the like.

In some embodiments, the processing of data from blocks 310, 320, 330 and 340 may include an internal transmission of calibrated sensor data and/or a certainty associated therewith to another algorithm of the sensor system, such as the alarming logic algorithm. For example, the alarm logic may determine when and how to alarm based on a level of certainty of the glucose value. Additionally or alternatively, the alarm logic may use a range or distribution of glucose values to select a most clinically conservative or least annoying alarming scheme, depending on certain user selectable or non-user selectable settings.

In some embodiments, the processing of data from blocks 310, 320, 330 and 340 may include displaying calibrated sensor data, wherein the display provides an indication or representation of the level of certainty of the sensor data, for example by changing color, resolution, range of sensor data and/or other displayable feature based on the level of certainty of the calibrated sensor data.

In some embodiments, the processing of data from blocks 310, 320, 330 and 340 may include altering the calibration process (algorithm). For example, when a high level of certainly is determined with respect to certain a priori, a posteriori and/or internally-derived calibration information, then certain other externally-derived calibration information (e.g., BG input from the user) may be relied upon less or not at all; namely, a sensor system may be configured to adaptively reduce or remove the reliance on and/or reduce remove the requirement for, BG input from external reference sources (e.g., finger stick tests).

In some embodiments, by looking at calibration information in relation to other related calibration information, improved adjusting of the a posteriori calibration information and/or calibration of the sensor may be obtained; for example, where certain distributions are tighter as compared to other distributions, certain real-time inputs may be requested to strategically improve the a posteriori distribution information. In one such example, wherein a posteriori sensitivity distribution information is tighter (a distribution with a higher level of certainty) is determined relative to a posteriori baseline distribution information (a distribution with a lower level of certainty), further processing could include intelligent requesting of a BG value with the user's glucose is low, whereby additional baseline information may be obtained in order to further tighten the baseline distribution information in a subsequent calibration process. In another embodiment further processing could include requesting BG values at less frequent intervals when the calibration parameters have reached a within the certainty level required for glycemic control.

In an exemplary embodiment, a sensor session may be calibrated with real time BG value input at a predetermined time period or interval (e.g., every 12 hours). However, after one or more calibrations (e.g., after three real-time BG inputs by the user), and optionally after the a priori calibration distribution information being tightened a posteriori, and a predetermined level of certainty (e.g., achieved with the a priori and/or a posteriori calibration distribution information), then a user will no longer be required or prompted to enter a BG input for calibration, after which the processor module relies solely on a priori, a posteriori and/or internally-derived information for future calibration of the sensor data, without further external reference input, such as described in U.S. Patent Publication No. 2012-0265035-A1, which is incorporated herein by reference in its entirety.

In an exemplary embodiment, a sensor session may be initiated and calibrated solely without external reference input, i.e., based on a priori calibration distribution information, and also optionally internally-derived real-time input, however based on a level of certainty of the calibration information (and/or resulting calibrated sensor data) meeting one or more criteria (e.g., level of certainty not exceeding a threshold), the processor module is configured to initiate a requirement for BG input (or to use existing BG values) for the calibration process. For example, at the sensor session start up, the processor module is configured to calibrate the sensor data without reference BG input, and the resulting calibrated sensor data compared to a reference BG value provided by the user; if the calibrated sensor data and reference BG value meet a criterion (e.g., are not sufficiently concordant), then the BG value may be needed (i.e., used in the calibration process), and future calibrations may require BG input; however if the if the calibrated sensor data and reference BG value meet another criterion (e.g., are sufficiently concordant), then the BG value input is not needed (i.e., used in a calibration process), and future calibrations may not require BG input.

Although examples described above illustrate BG input as an input useful for determining a level of certainty using information determined at block 320, other real-time inputs, including internally-derived real-time data, externally-derived real-time data, and combinations of internally- and/or externally-derived real-time data described in more detail elsewhere herein may also be used to for determining a level of certainty.

Additionally or alternatively, a level of certainty may be determined from a priori calibration distribution information from block 310, such as in embodiment wherein the a priori calibration distribution information is a feedback of a posteriori calibration distribution information from a previous calibration, then a level of certainty may be determined based on the a priori calibration distribution information, for example based on the level of (tightness or looseness) of distribution, which may be quantified by standard deviations, confidence intervals, or the like. As another example, in embodiments wherein the a priori calibration distribution information is sensor specific, e.g., based on a manufacturing code or other sensor specific information, the processor module may be configured to determine a level of certainty therefrom.

Additionally or alternatively, a level of certainty may be determined from a posteriori calibration distribution information from block 330, for example based on the level of (tightness or looseness) of distribution, which may be quantified by standard deviations, confidence intervals, or the like.

Additionally or alternatively, a level of certainty may be determined from the process at block 340. In one example, wherein a probability analysis is applied to convert at least one sensor data point into calibrated sensor data, the probability function inherently provides a level of probability or certain associated with the "most probable" result. As used herein, certainty generally refers to a level of confidence in the calibrated sensor data, for example, a positive or negative reliance on the data (e.g., for calibration, display, and the like), a rating (e.g., of at least 60%, 70%, 80%, 90% or 100% confidence thereon), and/or other processing of the sensor data.

In some embodiments, the level of certainty may be used for decision making of display, calibration, alarming, sensor health/diagnostics, insulin delivery, and the like. In some embodiments, processor module 214 is configured to control an output based at least in part on the level of certainty at block 350 based on data from any of blocks 310, 320, 330 and/340. In some embodiments, the system 8 is configured to control a display (e.g., a user interface) based at least in part on the level of certainty at block 350 based on data from any of blocks 310, 320, 330 and/or 340. In some embodiments, the system 8 is configured to control the display of raw and/or filtered data, or a level of filtered data, (e.g., on a user interface or display) based at least in part on the level of certainty at block 350 based on data from any of blocks 310, 320, 330 and/or 340. In some embodiments, the system 8 is configured to display rate of change information based at least in part on the level of certainty at block 350 based on data from any of blocks 310, 320, 330 and/or 340. In some embodiments, the system 8 is configured to control alarms indicative of at least one of hypoglycemia, hyperglycemia, predicted hypoglycemia, and/or predicted hyperglycemia based at least in part on the level of certainty at block 350 based on data from any of blocks 310, 320, 330 and/or 340. In some embodiments, the system 8 is configured to control insulin delivery and/or insulin therapy instructions based at least in part on the level of certainty at block 350 based on data from any of blocks 310, 320, 330 and/or 340, for example, when to fall back to a more conservative recommendation or when to open the loop (e.g., request user interaction) of a closed loop insulin delivery system. In some embodiments, the system 8 is configured to send certainty information to an insulin delivery device at block 350 based on data from any of blocks 310, 320, 330 and/or 340, for example, a glucose value and certainty interval around the glucose value. In some embodiments, the system 8 is configured to diagnose a sensor condition at block 350 based at least in part on the level of certainty based on data from any of blocks 310, 320, 330 and/or 340. In some embodiments, the system 8 is configured to suspend display of sensor data based at least in part on the level of certainty at block 350 based on data from any of blocks 310, 320, 330 and/or 340. In some embodiments, the system 8 is configured to shut down a sensor session based at least in part on the level of certainty at block 350 based on data from any of blocks 310, 320, 330 and/or 340. In some embodiments, the system 8 is configured ask the user for additional input (e.g., reference glucose value, meal information, exercise information, or the like) based at least in part on the level of certainty at block 350 based on data from any of blocks 310, 320, 330 and/or 340.

In some embodiments, processor module 214 may be configured to provide output of calibrated sensor data, for example, the output can be provided via a user interface, including but not limited to, visually on a screen, audibly through a speaker, or tactilely through a vibrator. Additionally, output can be provided via wired or wireless connection to an external device, including but not limited to, phone, cloud, computer, laptop, server, personal digital assistant, insulin delivery device, medical device, or other device that can be useful in interfacing with the CGM system, as described above with reference to the sensor system 8.

In some embodiments, when a predetermined increase or plateau in the level of certainty is achieved (e.g., a certain number of externally derived real-time inputs are in agreement with the calibration distribution information), then the processor module may be configured to reduce or remove a requirement for externally derived real-time input from the user, thereby allowing a system to adaptively switch from a reliance on externally derived real time input for calibration to a factory calibration (i.e., wherein the system relies solely on internally derived information for calibration). In some embodiments, when a predetermined decrease in the level of certainty is achieved (e.g., a certain number of internally derived real-time inputs are in agreement with the calibration distribution information), then the processor module may be configured to switch from a factory calibration to a newly initiated or increased requirement for external real-time input from the user, thereby allowing a system to adaptively switch from a factory calibration (i.e., wherein the system relies solely on internally derived information for calibration) to a calibration based on externally derived real time input. One skilled in the art appreciated that hybrids between factory calibration and calibration based on externally derived real time input is possible, where the reliance on one or the other is not all or nothing, but rather degrees in between. In some embodiments the processor module may be configured to reduce or remove a requirement for externally derived real-time input from the user when the current calibrations distribution substantially agree with calibration distributions from sensors used in a previous time window (such as three weeks or six months).

In some embodiments, when a predetermined decrease in the level of certainty is identified (e.g., based on end of life criteria or broadening of the sensitivity or sensor drift distribution information), which may be indicative of end of life for example, then the processor module may be configured to initiate or increase a requirement for externally derived real-time input from the user. Similarly, if a consistently low level of certainty (e.g., based on sensor failure criteria) is determined by the processor module, then a sensor failure may be identified.

A plurality of examples follow that describe flowchart 300 in further detail. These examples are not meant to be limiting in any way, but merely serve to illustrate how the various operations of flowchart 300 may be achieved.

Example 1

Adjusting distributions of sensitivity and/or baseline. Some conventional continuous glucose monitoring data processing relies on the assumption that BG inputs (e.g., assuming they pass certain outlier criteria) are accurate. For example, the calibration parameters are estimated with least-squares regression that assumes there are no errors in the reference values. In contrast, some of the disclosed embodiments recognize that the BG inputs may be neither right nor wrong, but rather represent a range of possible values (including erroneous values), and may be useful to adjust the distribution of sensitivity and/or baseline.

At block 310, a priori calibration distribution information is received from e.g., the sensor system. In the present example, the a priori distribution information includes a distribution for m and b, as illustrated in FIG. 4 and FIG. 5.

At block 320, one or more real-time inputs that may influence sensor calibration are received. In the present example, the real-time input is a BG input provided by the user via e.g. the finger stick method.

At block 330, the a priori distribution of sensitivity and/or baseline is adjusted based on the BG value to produce an a posteriori distribution of sensitivity and/or baseline. For example, a tighter distribution and/or shifted distribution for m may result if the glucose is high (based on the matched data pair information). As another example, a tighter distribution for b may result if the glucose is low (based on the matched pair information). In some embodiments, the a posteriori distributions of m and b both change with each BG input and the correlation between m and b is also updated accordingly. For example, a calibration set with only one matched pair of data can have a correlated set of m and b values that are substantially equivalent in fit quality.

Although this example describes adjusting the a priori calibration distribution itself to form the a posteriori calibration distribution information, the a priori calibration distribution information need not be adjusted; rather, the a posteriori calibration information may be considered the combination of the a priori calibration distribution information from block 310 and the real-time input(s), which include distribution or range information, from block 320 that together form a posteriori calibration distribution information (e.g., a posteriori array of information). For example, if the BG value is 130 mg/dL, the BG value may be assigned a range of values, such as 130±15%. This assignment of ranges may be based on the certainty or uncertainty in the measured or derived value (determined in real-time and/or based on a priori calibration distribution information). In such embodiments as when BG has a range of values, the BG range (or alternatively associated matched data pair range) may be used to adjust the a priori distribution of sensitivity and/or baseline to create an a posteriori distribution.

If the BG value is reading of 130 mg/dL (on the meter), but the user accidentally enters the value 310 mg/dL into the sensor interface/system. This may be caught by outlier detection methods (a real time input of block 320), however, in contrast to conventional systems that might throw away the outlier, this example allows for the possibility of the BG to be considered and used in a probability analysis. To do this, the probability distribution assigned to a user-entered blood glucose values may be assumed to be a weighted combination of the random error distribution of a correctly-used meter (e.g., 15%) and a secondary error distributions that describes a wider range of possible value that result when the blood glucose meter is used incorrectly or there are data entry errors.

At block 340, the processor module is configured to use a probability analysis to determine a most probable sensitivity and baseline based on the a posteriori calibration distribution information and that most probable sensitivity and baseline used to convert the uncalibrated sensor data into calibrated sensor data using conventional regression.

At block 350, a certainty level is assigned to the new m and b values based on the confidence interval determined from the probability analysis. For example, if the distributions of the m and b values are tight distributions and the BG value taken occurs on day 4 of sensor use, so that the BG value only shift or tightens the distributions slightly, it can be inferred that there is high confidence in the new m and b values.

Example 2

Adaptive boundaries for sensitivity and/or baseline. Some conventional calibration checks include the use of upper and/or lower boundaries to discern whether the calibrated data falls within an acceptable range or zone. These upper and lower boundaries may be a priori information and may be used to guide or validate the baseline (b) and/or sensitivity (m) determined from the regression analysis. This can be useful in situations wherein regression results in errant sensitivity or baseline values. For example, when points (matched pairs) used for regression are too close in their reference values (i.e. not enough glucose range in the calibration), the resulting regression statistically is less accurate than when the values are spread farther apart. As another example, a sensor that is not properly deployed or is damaged during deployment can yield a skewed or errant baseline signal.

FIG. 10 is a graph that illustrates predetermined acceptable upper and lower boundaries for sensitivity and baseline, which are a priori calibration distribution information in this example. The x-axis represents reference glucose data (blood glucose) from a reference glucose source in mg/dL; the y-axis represents sensor data from a transcutaneous glucose sensor of the preferred embodiments in counts. An upper boundary line 815 is a line that represents an upper boundary of "acceptability" in this example; the lower boundary line 816 is a line that represents a lower boundary of "acceptability" in this example. The boundary lines 815, 816 were obtained from a retrospective analysis of in vivo sensitivities and baselines of glucose sensors.

A plurality of matched data pairs 817 represent data pairs in a calibration set obtained from a glucose sensor. The matched data pairs are plotted according to their sensor data and time-corresponding reference glucose data. A regression line 818 represents the result of regression of the matched data pairs 817 using least squares regression. In this example, the regression line falls within the upper and lower boundaries 815, 816 indicating that the sensor calibration is acceptable.

Ideally, the boundaries are set such that working sensors are calibrated accurately and easily (with two points), and non-working sensors are prevented from being calibrated. If the boundaries are drawn too tightly, a working sensor may not enter into calibration. Likewise, if the boundaries are drawn too loosely, the scheme can result in inaccurate calibration or can permit non-working sensors to enter into calibration.

In this calibration check, the upper and lower boundaries (e.g., wedge) are set at initial calibration (i.e., a priori calibration distribution information) and dynamically change (i.e., a posteriori) based on the real-time inputs. As time passes, and as calibration lines shift, the initial boundaries may not be as acceptable, which would result in false failures due to lack of adaptation of the boundaries to real-time inputs. Consequently, the present example provides for a dynamically changing set of boundaries. For example, the boundary parameters may be adjusted based on glucose concentration (as an exemplary real-time input).

At block 310, a priori calibration distribution information is received. In the present example, the a priori distribution information includes the boundary parameters, as illustrated in FIG. 10.

At block 320, one or more real-time inputs that may influence sensor calibration are received. In the present example, the real-time input is a BG input provided by the user via e.g. the finger stick method. The BG value is low (e.g., 80 mg/dL), indicating that there is a measurable baseline component. In this example, a boundary parameters (or baseline) algorithm or function is provided that uses the BG value as an input to determine baseline information and/or boundary parameters. Such a boundary algorithm uses the real-time input (e.g., blood glucose values or BG input), and estimate a baseline %. Thereafter, the baseline % may be used as a multiplier with sensor data (e.g., counts) to produce a baseline value. The baseline value may be used, in some embodiments, to update where a boundary may be centered. Certain assumptions may be used in determining or selecting the baseline function, including: 1) baseline is a parameter that remains stable enough to be considered constant after a predetermined time period, e.g., a few hours; and 2) BG values entered are fairly accurate.

In this example, the boundary algorithm includes two steps: (1) For each BG in a calibration set (for the array n×2, BGs and sensor counts), calculate the amount of baseline present in that signal (e.g., resulting in an array (n×1) of percentages); and (2) take the median of the array obtained by multiplying the percentages from Step 1 and the time matched sensor counts in the calibration set to obtain a baseline value. Use this baseline value to re-center the boundary parameters around this baseline.

It may be noted that using the baseline function described herein may be used to account for the relationship when the sensor has a high or low baseline. For example, if the calibration set reaches a certain limit (e.g., 6 points), 3 of those points can be utilized to estimate a baseline. A percentage of the output baseline and the time matched sensor counts of the 3 points (not used to estimate the baseline) may be calculated and then the BG values may be calculated. The curve that minimizes the error across the 3 BGs not used for the initial baseline estimation may then be used to explain the relationship between BGs and baseline signal.

At block 330, the a priori boundary parameters may be adjusted based on the BG value or related baseline value to produce an a posteriori calibration distribution (i.e., adjusted boundary parameters). For example, referring again to FIG.

19, the boundary parameters may be shifted if the BG value indicates that the older boundary parameters are no longer a good fit. Alternatively, a set of new boundary parameters may be calculated using the BG value and boundary algorithm to produce the a posteriori calibration distribution. In some embodiments, the a posteriori distribution calculated from the boundary algorithm may actually be a new set of boundary parameters that may be used in place of the a priori boundary parameters. In some embodiments, the a priori boundary parameters are adjusted by taking an average of the a priori boundary parameters and new boundary parameters determined using e.g., a boundary algorithm. An example improvement of a posteriori boundary parameters compared to a priori boundary parameters can be seen in FIG. 19.

At block 340, an acceptable regression line (i.e., on that fits within the a posteriori calibration distribution acceptable boundaries for m and b and the resulting transformation function is applied to at least one sensor data point to convert uncalibrated sensor data into calibrated sensor data.

At block 350, the calibrated sensor data is displayed on a user interface.

Example 3

Increasing or decreasing reliance on BG input based on a level of certainty. Some conventional continuous glucose monitoring data processing relies on the assumption that factory calibration information is accurate. However, it is known that over the life of a sensor, the sensor may begin to show signs of use and/or wear. For example, it has been found that a sensor's sensitivity to analyte concentration during a sensor session may change or drift as a function of time.

Consequently, the initial calibration or factory derived calibration may become less accurate as the life of the sensor progresses. In some embodiments, an additional factor may be considered: the "change in drift rate over time", or more precisely the "second derivative of sensitivity (or baseline) with respect to time", ddm/ddt or ddb/ddt. This essentially measures the rate of change in drift rate. For example, a sensor that steadily drifts throughout the wear period would have ddm/ddt=0, but a sensor that does not drift initially but then begins to would have a nonzero ddm/ddt value.

Again it is assumed that there is some probability distribution of ddm/ddt and ddb/ddt. In one example, a sensitivity or baseline drift profile may be may be used. Because sensitivity and baseline are not considered static values, but rather are considered functions of time, assuming some drift, the term "trajectory" may be a better descriptor. Thus, some of the disclosed embodiments recognize that factory calibration information may be more or less probable in certain circumstances, for example, relying more on BG input than factory calibration info (a priori calibration distribution information) when error at calibration is high in a certain direction at day 6 (e.g., there is trended error at calibration after the sensor has been in use for some time).

At block 310, a priori calibration distribution information is received from e.g., the factory-provided information stored in the sensor. The factory-provided information may be factory-derived information from a similar lot of sensors, information from a similar group of patients, etc. In the present example, the a priori distribution information includes sensitivity and/or baseline information, for example such as illustrated and described with respect to any of FIGS. 4-9.

At block 320, one or more real-time inputs that may influence sensor calibration are received from e.g., the sensor. In the present example, the real-time input is a BG input provided by the user on day 6 via e.g., the finger stick method. The BG input may be assigned a range of values, as explained in the discussion of FIG. 14. In some embodiments, the probability distributions or the BG input and/or the sensor signal are adjust as a function of the signal magnitude, rate of change, or direction of change. The BG input is associated with an error of greater than e.g., 20% over the last 12 hours, when comparing an the BG input with a time corresponding calibrated glucose value. This error may be indicative of a downward sensitivity shift on day 6.

At block 330, the a priori distribution of sensitivity is adjusted based on the BG to produce an a posteriori distribution for sensitivity. In some embodiments, the system 8 may adaptively weight the factory-derived distribution of m against the new BG information. For example, the factory-derived information may be assigned a wider distribution (e.g., indicating less confidence or certainty), while the newly obtained information may be assigned a narrower distribution (indicating more confidence or certainty).

In the present example, at block 330, the distribution of m is widened based on the trended error at calibration (as represented by the BG error). Conversely, the range of values for the BG inputs may be tightened.

At block 340, a new sensitivity is selected from the a posteriori distribution. The newly selected m may be selected based on e.g., probability analysis from the a posteriori distribution, similar as described above in EXAMPLE 1. In some embodiments, a new baseline is also selected from an a posteriori distribution. A transformation function using the newly selected sensitivity and/or baseline is applied to at least one sensor data point to convert uncalibrated sensor data into calibrated sensor data.

Figure 20:
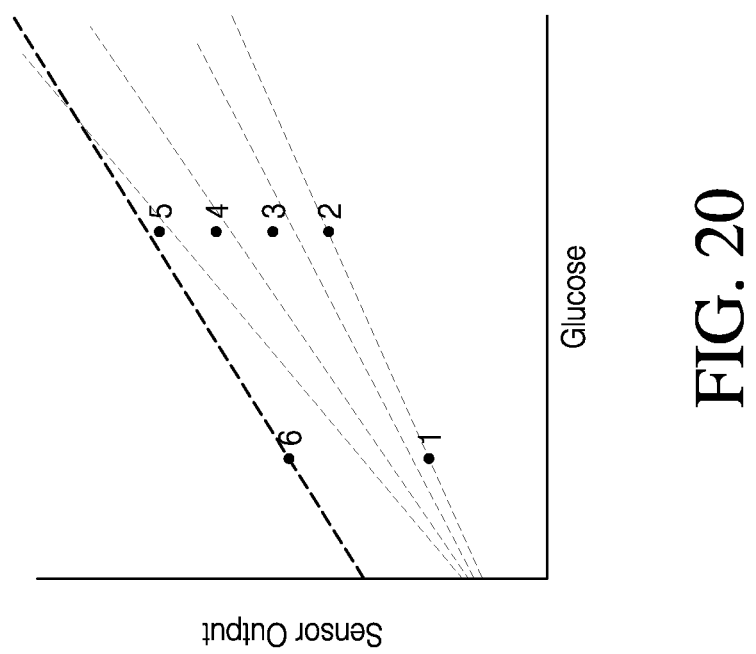
FIG. 20 is a graph of prospective calibration lines calculated throughout a sensor session that illustrates how the calibration may change over time during sensor wear in some embodiments.

In some embodiments, the analysis may depend heavily on the probability distributions, but the prospective calibration lines throughout the wear period may ideally look similar to the graph shown in FIG. 20, which much more accurately represents the actual calibration. It should be appreciated that newer points (e.g. BG values) are automatically given more "weighting" because of accounting for drift. In some embodiments, when point 3 is received, it not clear whether the discrepancy is due to noise or drift, but by the time point 4 is received; the function may favor a low ddm/ddt and ddb/ddt, and may assume that the drift it already detected continues. Finally, when the function receives point 6, it may recognize that this was most likely a steady baseline drift (as opposed to sensitivity drift) and can quickly accommodate that to give a very accurate final calibration line.

At block 350, a certainty level is assigned to the factory-derived sensitivity and/or baseline values. As will be appreciated, in the present example, the certainty level implies a reduced confidence in the factory (a priori) calibration information, which certainty level may be used as an input into other applications (e.g., using the factory-derived calibration information as an input into end of life analysis, as described in Ser. No. 13/733,742, entitled "End of Life Detection for Analyte Sensors", and filed on Jan. 3, 2013, which is incorporated herein by reference in its entirety.

Example 4 illustrates a Bayesian Learning Approach for Drift Estimation and Correction. In this example, sensors are manufactured with glucose sensitivity of a predetermined value and/or within a predetermined range, which may be determined from an in vitro test by the manufacturer. In this example, the sensor design exhibits a characteristic sensitivity profile; namely, after sensor insertion, the sensors begin at an initial sensitivity that is higher than the in vitro sensitivity because of changes in the sensor properties after insertion, after which this sensitivity increases and reaches a steady state value between days 4 and 7 (post sensor insertion).

Figure 21:
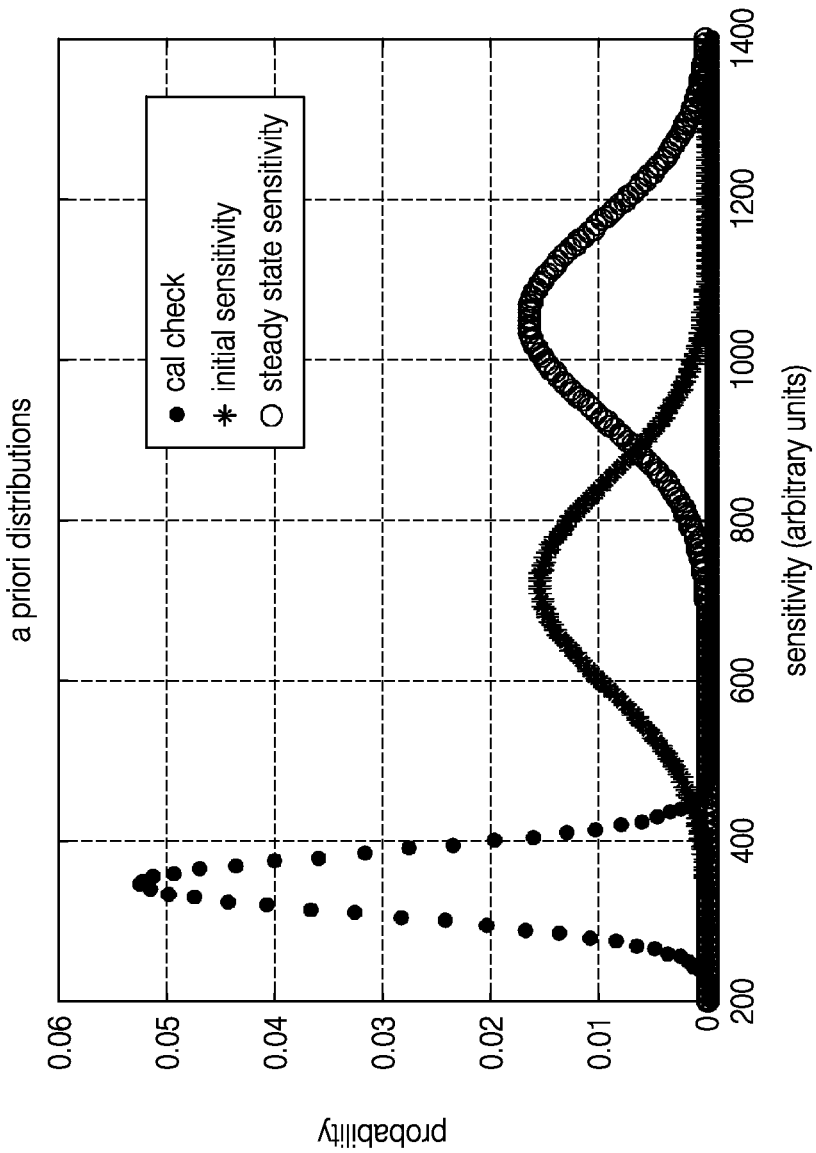
FIG. 21 is a graph of sensitivity distributions in one example, including a factory derived sensitivity distribution, an initial sensitivity distributions and a steady sensitivity distribution.
Figure 22:
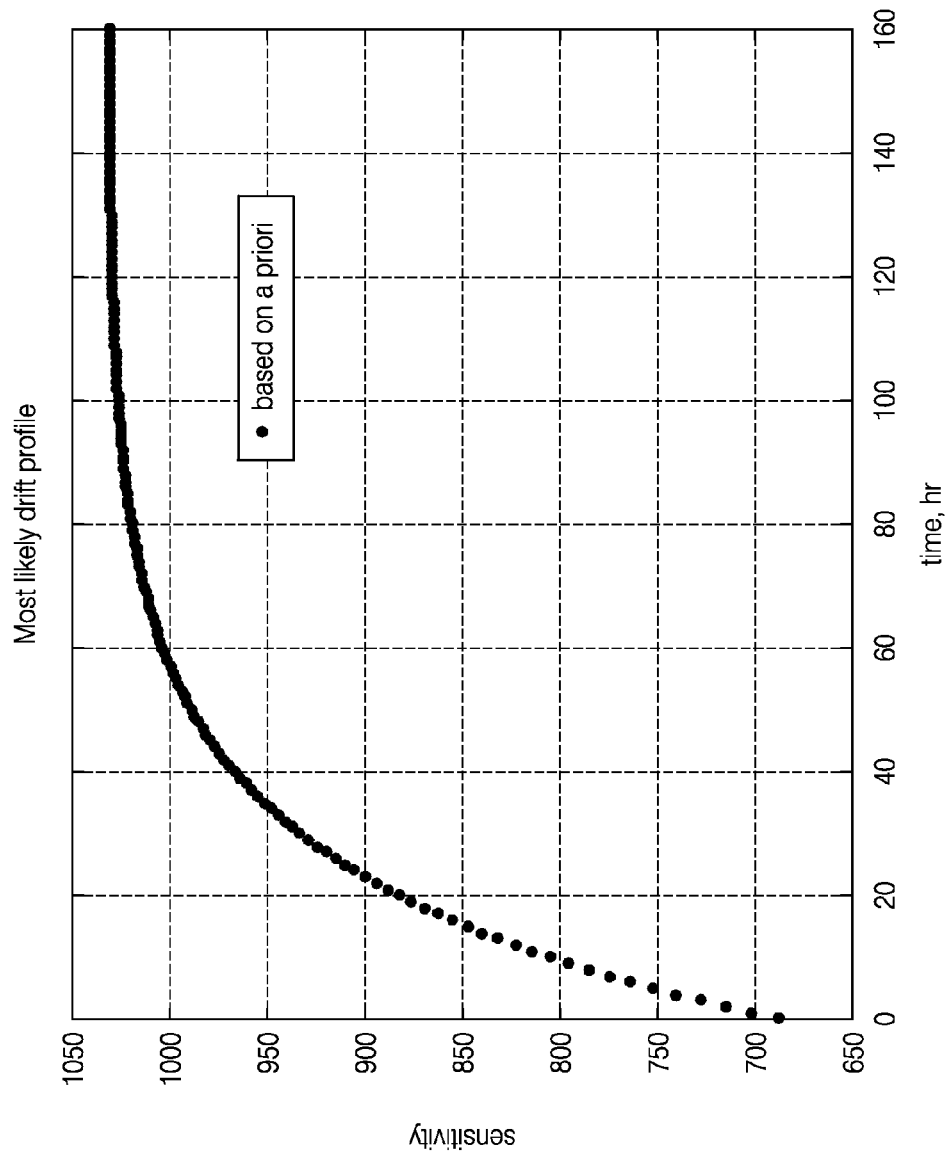
FIG. 22 is a graph that illustrates a drift profile over time in the example.

At block 310, the processor module is configured to generate a priori calibration distribution information, based on the in vitro sensitivity, including initial sensitivity distributions and steady sensitivity distributions, such as illustrated in FIG. 21. In FIG. 21, the x-axis represents sensitivity and the y-axis represents probability. Cal check values are sensitivity values derived in vitro (i.e., at the factory), initial sensitivity values are the initial sensitivity distributions and final sensitivity values are the steady state sensitivity distributions. Using the knowledge that sensor sensitivity changes over time from the time of insertion (i.e., drift), a drift profile may be modeled using exponential functions, e.g., sensitivity(t)=final_sensitivity−(final_sensitivity−initial_sensitivity)*exp(−t/τ), which is illustrated in FIG. 22. FIG. 22 is a graph that illustrates a drift profile over time; the x-axis represents time in hours and the y-axis represents sensitivity in arbitrary units.

At block 320, the sensitivity is measured (e.g., based on a BG input, an impedance value and/or other methods for measuring sensitivity). The real-time measurement of the initial sensitivity value may be compared to the most likely estimate for the initial sensitivity, and if the measured value differs from the estimated value by a predetermined amount, the processor module is configured to adaptively adjust the drift profile in real-time.

Figure 23:
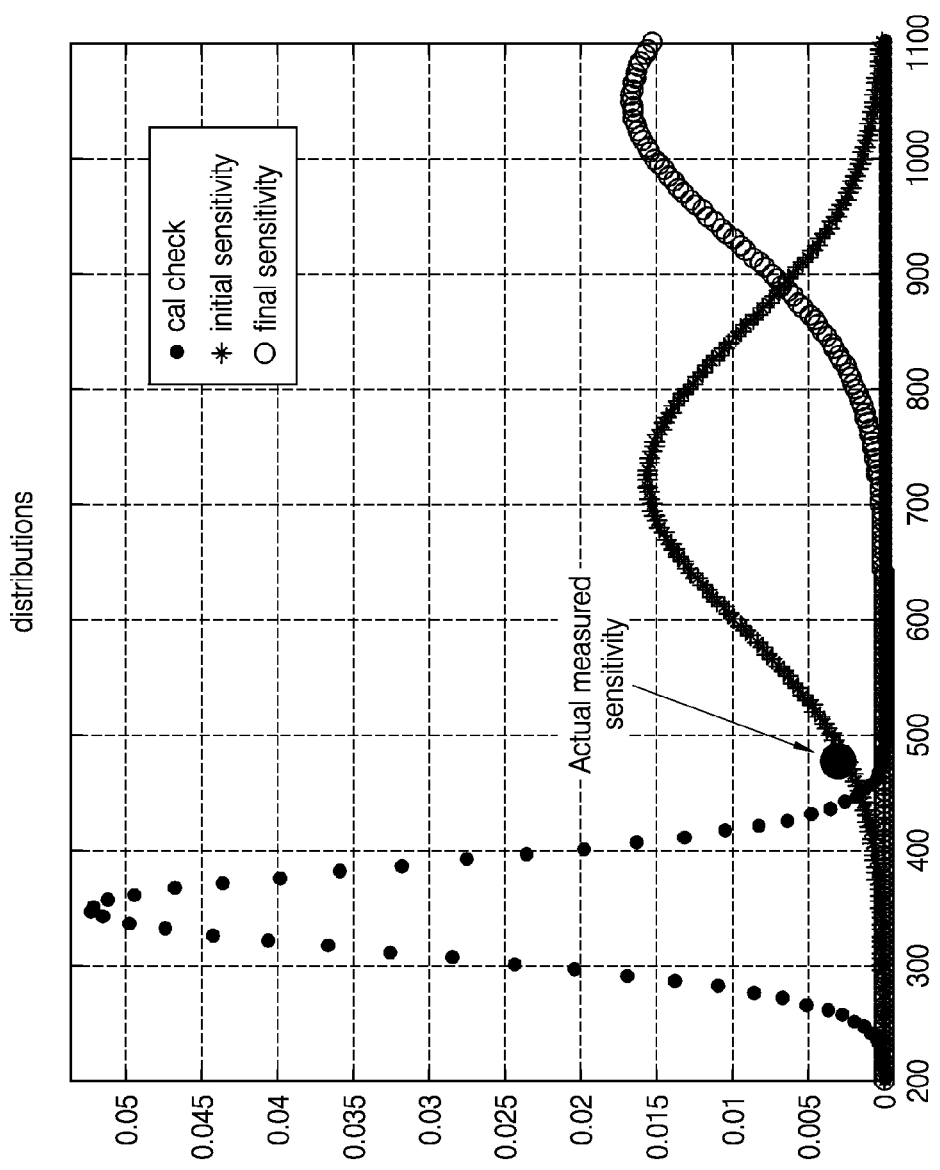
FIG. 23 is a graph similar to FIG. 21, but showing an actual initial sensitivity measurement (after sensor insertion) in the example.
Figure 24:
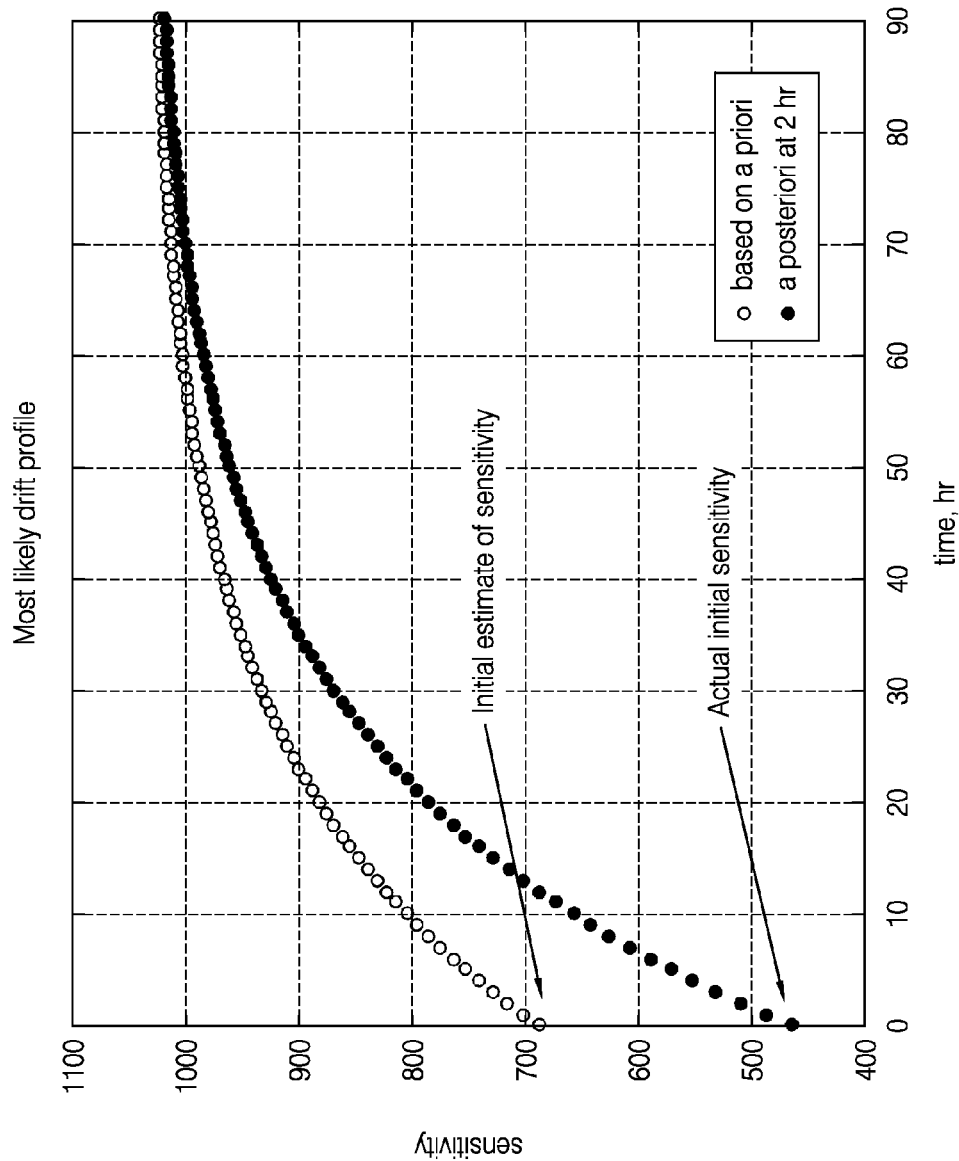
FIG. 24 is a graph that illustrates a drift profile similar to FIG. 22, however showing an adjustment of the drift profile, a posteriori, based on the actual measure sensitivity in the example.

FIG. 23 is a graph similar to FIG. 21, but showing an actual initial sensitivity measurement (after sensor insertion). Based on the initial actual sensitivity measurement (after sensor insertion), the processor module may be configured to adjust the a priori distribution of initial sensitivity (i.e., form an a posteriori distribution of initial sensitivity, not shown) after calculating the initial sensitivity. The sensor drift profile may also be re-evaluated and adjusted accordingly. FIG. 24 is a graph that illustrates a drift profile similar to FIG. 22, however showing an adjustment of the drift profile, a posteriori, based on the actual measure sensitivity. It should be appreciated that as the sensor session continues, and additional real-time inputs are received, the drift profiles can be continuously adjusted to correct the sensor sensitivity and the estimated glucose values.

Embodiments of the present disclosure are described above and below with reference to flowchart illustrations of methods, apparatus, and computer program products. It will be understood that each block of the flowchart illustrations, and combinations of blocks in the flowchart illustrations, can be implemented by execution of computer program instructions. These computer program instructions may be loaded onto a computer or other programmable data processing apparatus (such as a controller, microcontroller, microprocessor or the like) in a sensor electronics system to produce a machine, such that the instructions which execute on the computer or other programmable data processing apparatus create instructions for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks presented herein.

It should be appreciated that all methods and processes disclosed herein may be used in any glucose monitoring system, continuous or intermittent. It should further be appreciated that the implementation and/or execution of all methods and processes may be performed by any suitable devices or systems, whether local or remote. Further, any combination of devices or systems may be used to implement the present methods and processes. Methods and devices that are suitable for use in conjunction with aspects of the preferred embodiments are disclosed in U.S. Pat. Nos. 4,757,022; 4,994,167; 6,001,067; 6,558,321; 6,702,857; 6,741,877; 6,862,465; 6,931,327; 7,074,307; 7,081,195; 7,108,778; 7,110,803; 7,134,999; 7,136,689; 7,192,450; 7,226,978; 7,276,029; 7,310,544; 7,364,592; 7,366,556; 7,379,765; 7,424,318; 7,460,898; 7,467,003; 7,471,972; 7,494,465; 7,497,827; 7,519,408; 7,583,990; 7,591,801; 7,599,726; 7,613,491; 7,615,007; 7,632,228; 7,637,868; 7,640,048; 7,651,596; 7,654,956; 7,657,297; 7,711,402; 7,713,574; 7,715,893; 7,761,130; 7,771,352; 7,774,145; 7,775,975; 7,778,680; 7,783,333; 7,792,562; 7,797,028; 7,826,981; 7,828,728; 7,831,287; 7,835,777; 7,857,760; 7,860,545; 7,875,293; 7,881,763; 7,885,697; 7,896,809; 7,899,511; 7,901,354; 7,905,833; 7,914,450; 7,917,186; 7,920,906; 7,925,321; 7,927,274; 7,933,639; 7,935,057; 7,946,984; 7,949,381; 7,955,261; 7,959,569; 7,970,448; 7,974,672; 7,976,492; 7,979,104; 7,986,986; 7,998,071; 8,000,901; 8,005,524; 8,005,525; 8,010,174; 8,027,708; 8,050,731; 8,052,601; 8,053,018; 8,060,173; 8,060,174; 8,064,977; 8,073,519; 8,073,520; 8,118,877; 8,128,562; 8,133,178; 8,150,488; 8,155,723; 8,160,669; 8,160,671; 8,167,801; 8,170,803; 8,195,265; 8,206,297; 8,216,139; 8,229,534; 8,229,535; 8,229,536; 8,231,531; 8,233,958; 8,233,959; 8,249,684; 8,251,906; 8,255,030; 8,255,032; 8,255,033; 8,257,259; 8,260,393; 8,265,725; 8,275,437; 8,275,438; 8,277,713; 8,280,475; 8,282,549; 8,282,550; 8,285,354; 8,287,453; 8,290,559; 8,290,560; 8,290,561; 8,290,562; 8,292,810; 8,298,142; 8,311,749; 8,313,434; 8,321,149; 8,332,008; 8,346,338; 8,364,229; 8,369,919; 8,374,667; 8,386,004; and 8,394,021.

Methods and devices that are suitable for use in conjunction with aspects of the preferred embodiments are disclosed in U.S. Patent Publication No. 2003-0032874-A1; U.S. Patent Publication No. 2005-0033132-A1; U.S. Patent Publication No. 2005-0051427-A1; U.S. Patent Publication No. 2005-0090607-A1; U.S. Patent Publication No. 2005-0176136-A1; U.S. Patent Publication No. 2005-0245799-A1; U.S. Patent Publication No. 2006-0015020-A1; U.S. Patent Publication No. 2006-0016700-A1; U.S. Patent Publication No. 2006-0020188-A1; U.S. Patent Publication No. 2006-0020190-A1; U.S. Patent Publication No. 2006-0020191-A1; U.S. Patent Publication No. 2006-0020192-A1; U.S. Patent Publication No. 2006-0036140-A1; U.S. Patent Publication No. 2006-0036143-A1; U.S. Patent Publication No. 2006-0040402-A1; U.S. Patent Publication No. 2006-0068208-A1; U.S. Patent Publication No. 2006-0142651-A1; U.S. Patent Publication No. 2006-0155180-

A1; U.S. Patent Publication No. 2006-0198864-A1; U.S. Patent Publication No. 2006-0200020-A1; U.S. Patent Publication No. 2006-0200022-A1; U.S. Patent Publication No. 2006-0200970-A1; U.S. Patent Publication No. 2006-0204536-A1; U.S. Patent Publication No. 2006-0224108-A1; U.S. Patent Publication No. 2006-0235285-A1; U.S. Patent Publication No. 2006-0249381-A1; U.S. Patent Publication No. 2006-0252027-A1; U.S. Patent Publication No. 2006-0253012-A1; U.S. Patent Publication No. 2006-0257995-A1; U.S. Patent Publication No. 2006-0258761-A1; U.S. Patent Publication No. 2006-0263763-A1; U.S. Patent Publication No. 2006-0270922-A1; U.S. Patent Publication No. 2006-0270923-A1; U.S. Patent Publication No. 2007-0027370-A1; U.S. Patent Publication No. 2007-0032706-A1; U.S. Patent Publication No. 2007-0032718-A1; U.S. Patent Publication No. 2007-0045902-A1; U.S. Patent Publication No. 2007-0059196-A1; U.S. Patent Publication No. 2007-0066873-A1; U.S. Patent Publication No. 2007-0173709-A1; U.S. Patent Publication No. 2007-0173710-A1; U.S. Patent Publication No. 2007-0208245-A1; U.S. Patent Publication No. 2007-0208246-A1; U.S. Patent Publication No. 2007-0232879-A1; U.S. Patent Publication No. 2008-0045824-A1; U.S. Patent Publication No. 2008-0083617-A1; U.S. Patent Publication No. 2008-0086044-A1; U.S. Patent Publication No. 2008-0108942-A1; U.S. Patent Publication No. 2008-0119703-A1; U.S. Patent Publication No. 2008-0119704-A1; U.S. Patent Publication No. 2008-0119706-A1; U.S. Patent Publication No. 2008-0183061-A1; U.S. Patent Publication No. 2008-0183399-A1; U.S. Patent Publication No. 2008-0188731-A1; U.S. Patent Publication No. 2008-0189051-A1; U.S. Patent Publication No. 2008-0194938-A1; U.S. Patent Publication No. 2008-0197024-A1; U.S. Patent Publication No. 2008-0200788-A1; U.S. Patent Publication No. 2008-0200789-A1; U.S. Patent Publication No. 2008-0200791-A1; U.S. Patent Publication No. 2008-0214915-A1; U.S. Patent Publication No. 2008-0228054-A1; U.S. Patent Publication No. 2008-0242961-A1; U.S. Patent Publication No. 2008-0262469-A1; U.S. Patent Publication No. 2008-0275313-A1; U.S. Patent Publication No. 2008-0287765-A1; U.S. Patent Publication No. 2008-0306368-A1; U.S. Patent Publication No. 2008-0306434-A1; U.S. Patent Publication No. 2008-0306435-A1; U.S. Patent Publication No. 2008-0306444-A1; U.S. Patent Publication No. 2009-0018424-A1; U.S. Patent Publication No. 2009-0030294-A1; U.S. Patent Publication No. 2009-0036758-A1; U.S. Patent Publication No. 2009-0036763-A1; U.S. Patent Publication No. 2009-0043181-A1; U.S. Patent Publication No. 2009-0043182-A1; U.S. Patent Publication No. 2009-0043525-A1; U.S. Patent Publication No. 2009-0045055-A1; U.S. Patent Publication No. 2009-0062633-A1; U.S. Patent Publication No. 2009-0062635-A1; U.S. Patent Publication No. 2009-0076360-A1; U.S. Patent Publication No. 2009-0099436-A1; U.S. Patent Publication No. 2009-0124877-A1; U.S. Patent Publication No. 2009-0124879-A1; U.S. Patent Publication No. 2009-0124964-A1; U.S. Patent Publication No. 2009-0131769-A1; U.S. Patent Publication No. 2009-0131777-A1; U.S. Patent Publication No. 2009-0137886-A1; U.S. Patent Publication No. 2009-0137887-A1; U.S. Patent Publication No. 2009-0143659-A1; U.S. Patent Publication No. 2009-0143660-A1; U.S. Patent Publication No. 2009-0156919-A1; U.S. Patent Publication No. 2009-0163790-A1; U.S. Patent Publication No. 2009-0178459-A1; U.S. Patent Publication No. 2009-0192366-A1; U.S. Patent Publication No. 2009-0192380-A1; U.S. Patent Publication No. 2009-0192722-A1; U.S. Patent Publication No. 2009-0192724-A1; U.S. Patent Publication No. 2009-0192751-A1; U.S. Patent Publication No. 2009-0203981-A1; U.S. Patent Publication No. 2009-0216103-A1; U.S. Patent Publication No. 2009-0240120-A1; U.S. Patent Publication No. 2009-0240193-A1; U.S. Patent Publication No. 2009-0242399-A1; U.S. Patent Publication No. 2009-0242425-A1; U.S. Patent Publication No. 2009-0247855-A1; U.S. Patent Publication No. 2009-0247856-A1; U.S. Patent Publication No. 2009-0287074-A1; U.S. Patent Publication No. 2009-0299155-A1; U.S. Patent Publication No. 2009-0299156-A1; U.S. Patent Publication No. 2009-0299162-A1; U.S. Patent Publication No. 2010-0010331-A1; U.S. Patent Publication No. 2010-0010332-A1; U.S. Patent Publication No. 2010-0016687-A1; U.S. Patent Publication No. 2010-0016698-A1; U.S. Patent Publication No. 2010-0030484-A1; U.S. Patent Publication No. 2010-0036215-A1; U.S. Patent Publication No. 2010-0036225-A1; U.S. Patent Publication No. 2010-0041971-A1; U.S. Patent Publication No. 2010-0045465-A1; U.S. Patent Publication No. 2010-0049024-A1; U.S. Patent Publication No. 2010-0076283-A1; U.S. Patent Publication No. 2010-0081908-A1; U.S. Patent Publication No. 2010-0081910-A1; U.S. Patent Publication No. 2010-0087724-A1; U.S. Patent Publication No. 2010-0096259-A1; U.S. Patent Publication No. 2010-0121169-A1; U.S. Patent Publication No. 2010-0161269-A1; U.S. Patent Publication No. 2010-0168540-A1; U.S. Patent Publication No. 2010-0168541-A1; U.S. Patent Publication No. 2010-0168542-A1; U.S. Patent Publication No. 2010-0168543-A1; U.S. Patent Publication No. 2010-0168544-A1; U.S. Patent Publication No. 2010-0168545-A1; U.S. Patent Publication No. 2010-0168546-A1; U.S. Patent Publication No. 2010-0168657-A1; U.S. Patent Publication No. 2010-0174157-A1; U.S. Patent Publication No. 2010-0174158-A1; U.S. Patent Publication No. 2010-0174163-A1; U.S. Patent Publication No. 2010-0174164-A1; U.S. Patent Publication No. 2010-0174165-A1; U.S. Patent Publication No. 2010-0174166-A1; U.S. Patent Publication No. 2010-0174167-A1; U.S. Patent Publication No. 2010-0179401-A1; U.S. Patent Publication No. 2010-0179402-A1; U.S. Patent Publication No. 2010-0179404-A1; U.S. Patent Publication No. 2010-0179408-A1; U.S. Patent Publication No. 2010-0179409-A1; U.S. Patent Publication No. 2010-0185065-A1; U.S. Patent Publication No. 2010-0185069-A1; U.S. Patent Publication No. 2010-0185070-A1; U.S. Patent Publication No. 2010-0185071-A1; U.S. Patent Publication No. 2010-0185075-A1; U.S. Patent Publication No. 2010-0191082-A1; U.S. Patent Publication No. 2010-0198035-A1; U.S. Patent Publication No. 2010-0198036-A1; U.S. Patent Publication No. 2010-0212583-A1; U.S. Patent Publication No. 2010-0217557-A1; U.S. Patent Publication No. 2010-0223013-A1; U.S. Patent Publication No. 2010-0223022-A1; U.S. Patent Publication No. 2010-0223023-A1; U.S. Patent Publication No. 2010-0228109-A1; U.S. Patent Publication No. 2010-0228497-A1; U.S. Patent Publication No. 2010-0240975-A1; U.S. Patent Publication No. 2010-0240976 C1; U.S. Patent Publication No. 2010-0261987-A1; U.S. Patent Publication No. 2010-0274107-A1; U.S. Patent Publication No. 2010-0280341-A1; U.S. Patent Publication No. 2010-0286496-A1; U.S. Patent Publication No. 2010-0298684-A1; U.S. Patent Publication No. 2010-0324403-A1; U.S. Patent Publication No. 2010-0331656-A1; U.S. Patent Publication No. 2010-0331657-A1; U.S. Patent Publication No. 2011-0004085-A1; U.S. Patent Publication No. 2011-0009727-A1; U.S. Patent Publication No. 2011-0024043-A1; U.S. Patent Publication No. 2011-0024307-A1; U.S. Patent Publication No. 2011-0027127-A1; U.S. Patent Publication No. 2011-

0027453-A1; U.S. Patent Publication No. 2011-0027458-A1; U.S. Patent Publication No. 2011-0028815-A1; U.S. Patent Publication No. 2011-0028816-A1; U.S. Patent Publication No. 2011-0046467-A1; U.S. Patent Publication No. 2011-0077490-A1; U.S. Patent Publication No. 2011-0118579-A1; U.S. Patent Publication No. 2011-0124992-A1; U.S. Patent Publication No. 2011-0125410-A1; U.S. Patent Publication No. 2011-0130970-A1; U.S. Patent Publication No. 2011-0130971-A1; U.S. Patent Publication No. 2011-0130998-A1; U.S. Patent Publication No. 2011-0144465-A1; U.S. Patent Publication No. 2011-0178378-A1; U.S. Patent Publication No. 2011-0190614-A1; U.S. Patent Publication No. 2011-0201910-A1; U.S. Patent Publication No. 2011-0201911-A1; U.S. Patent Publication No. 2011-0218414-A1; U.S. Patent Publication No. 2011-0231140-A1; U.S. Patent Publication No. 2011-0231141-A1; U.S. Patent Publication No. 2011-0231142-A1; U.S. Patent Publication No. 2011-0253533-A1; U.S. Patent Publication No. 2011-0263958-A1; U.S. Patent Publication No. 2011-0270062-A1; U.S. Patent Publication No. 2011-0270158-A1; U.S. Patent Publication No. 2011-0275919-A1; U.S. Patent Publication No. 2011-0290645-A1; U.S. Patent Publication No. 2011-0313543-A1; U.S. Patent Publication No. 2011-0320130-A1; U.S. Patent Publication No. 2012-0035445-A1; U.S. Patent Publication No. 2012-0040101-A1; U.S. Patent Publication No. 2012-0046534-A1; U.S. Patent Publication No. 2012-0078071-A1; U.S. Patent Publication No. 2012-0108934-A1; U.S. Patent Publication No. 2012-0130214-A1; U.S. Patent Publication No. 2012-0172691-A1; U.S. Patent Publication No. 2012-0179014-A1; U.S. Patent Publication No. 2012-0186581-A1; U.S. Patent Publication No. 2012-0190953-A1; U.S. Patent Publication No. 2012-0191063-A1; U.S. Patent Publication No. 2012-0203467-A1; U.S. Patent Publication No. 2012-0209098-A1; U.S. Patent Publication No. 2012-0215086-A1; U.S. Patent Publication No. 2012-0215087-A1; U.S. Patent Publication No. 2012-0215201-A1; U.S. Patent Publication No. 2012-0215461-A1; U.S. Patent Publication No. 2012-0215462-A1; U.S. Patent Publication No. 2012-0215496-A1; U.S. Patent Publication No. 2012-0220979-A1; U.S. Patent Publication No. 2012-0226121-A1; U.S. Patent Publication No. 2012-0228134-A1; U.S. Patent Publication No. 2012-0238852-A1; U.S. Patent Publication No. 2012-0245448-A1; U.S. Patent Publication No. 2012-0245855-A1; U.S. Patent Publication No. 2012-0255875-A1; U.S. Patent Publication No. 2012-0258748-A1; U.S. Patent Publication No. 2012-0259191-A1; U.S. Patent Publication No. 2012-0260323-A1; U.S. Patent Publication No. 2012-0262298-A1; U.S. Patent Publication No. 2012-0265035-A1; U.S. Patent Publication No. 2012-0265036-A1; U.S. Patent Publication No. 2012-0265037-A1; U.S. Patent Publication No. 2012-0277562-A1; U.S. Patent Publication No. 2012-0277566-A1; U.S. Patent Publication No. 2012-0283541-A1; U.S. Patent Publication No. 2012-0283543-A1; U.S. Patent Publication No. 2012-0296311-A1; U.S. Patent Publication No. 2012-0302854-A1; U.S. Patent Publication No. 2012-0302855-A1; U.S. Patent Publication No. 2012-0323100-A1; U.S. Patent Publication No. 2013-0012798-A1; U.S. Patent Publication No. 2013-0030273-A1; U.S. Patent Publication No. 2013-0035575-A1; U.S. Patent Publication No. 2013-0035865-A1; U.S. Patent Publication No. 2013-0035871-A1; U.S. Patent Publication No. 2005-0056552-A1; U.S. Patent Publication No. 2005-0182451-A1; U.S. Patent Publication No. 2013000536650A1; and U.S. Patent Publication No. 2013-0053666-A1.

Methods and devices that are suitable for use in conjunction with aspects of the preferred embodiments are disclosed in U.S. application Ser. No. 09/447,227 filed on Nov. 22, 1999 and entitled "DEVICE AND METHOD FOR DETERMINING ANALYTE LEVELS"; U.S. application Ser. No. 12/828,967 filed on Jul. 1, 2010 and entitled "HOUSING FOR AN INTRAVASCULAR SENSOR"; U.S. application Ser. No. 13/461,625 filed on May 1, 2012 and entitled "DUAL ELECTRODE SYSTEM FOR A CONTINUOUS ANALYTE SENSOR"; U.S. application Ser. No. 13/594,602 filed on Aug. 24, 2012 and entitled "POLYMER MEMBRANES FOR CONTINUOUS ANALYTE SENSORS"; U.S. application Ser. No. 13/594,734 filed on Aug. 24, 2012 and entitled "POLYMER MEMBRANES FOR CONTINUOUS ANALYTE SENSORS"; U.S. application Ser. No. 13/607,162 filed on Sep. 7, 2012 and entitled "SYSTEM AND METHODS FOR PROCESSING ANALYTE SENSOR DATA FOR SENSOR CALIBRATION"; U.S. application Ser. No. 13/624,727 filed on Sep. 21, 2012 and entitled "SYSTEMS AND METHODS FOR PROCESSING AND TRANSMITTING SENSOR DATA"; U.S. application Ser. No. 13/624,808 filed on Sep. 21, 2012 and entitled "SYSTEMS AND METHODS FOR PROCESSING AND TRANSMITTING SENSOR DATA"; U.S. application Ser. No. 13/624,812 filed on Sep. 21, 2012 and entitled "SYSTEMS AND METHODS FOR PROCESSING AND TRANSMITTING SENSOR DATA"; U.S. application Ser. No. 13/732,848 filed on Jan. 2, 2013 and entitled "ANALYTE SENSORS HAVING A SIGNAL-TO-NOISE RATIO SUBSTANTIALLY UNAFFECTED BY NON-CONSTANT NOISE"; U.S. application Ser. No. 13/733,742 filed on Jan. 3, 2013 and entitled "END OF LIFE DETECTION FOR ANALYTE SENSORS"; U.S. application Ser. No. 13/733,810 filed on Jan. 3, 2013 and entitled "OUTLIER DETECTION FOR ANALYTE SENSORS"; U.S. application Ser. No. 13/742,178 filed on Jan. 15, 2013 and entitled "SYSTEMS AND METHODS FOR PROCESSING SENSOR DATA"; U.S. application Ser. No. 13/742,694 filed on Jan. 16, 2013 and entitled "SYSTEMS AND METHODS FOR PROVIDING SENSITIVE AND SPECIFIC ALARMS"; U.S. application Ser. No. 13/742,841 filed on Jan. 16, 2013 and entitled "SYSTEMS AND METHODS FOR DYNAMICALLY AND INTELLIGENTLY MONITORING A HOST'S GLYCEMIC CONDITION AFTER AN ALERT IS TRIGGERED"; U.S. application Ser. No. 13/747,746 filed on Jan. 23, 2013 and entitled "DEVICES, SYSTEMS, AND METHODS TO COMPENSATE FOR EFFECTS OF TEMPERATURE ON IMPLANTABLE SENSORS"; U.S. application Ser. No. 13/779,607 filed on Feb. 27, 2013 and entitled "ZWITTERION SURFACE MODIFICATIONS FOR CONTINUOUS SENSORS"; U.S. application Ser. No. 13/780,808 filed on Feb. 28, 2013 and entitled "SENSORS FOR CONTINUOUS ANALYTE MONITORING, AND RELATED METHODS"; U.S. application Ser. No. 13/784,523 filed on Mar. 4, 2013 and entitled "ANALYTE SENSOR WITH INCREASED REFERENCE CAPACITY"; U.S. application Ser. No. 13/789,371 filed on Mar. 7, 2013 and entitled "MULTIPLE ELECTRODE SYSTEM FOR A CONTINUOUS ANALYTE SENSOR, AND RELATED METHODS"; U.S. application Ser. No. 13/789,279 filed on Mar. 7, 2013 and entitled "USE OF SENSOR REDUNDANCY TO DETECT SENSOR FAILURES"; U.S. application Ser. No. 13/789,339 filed on Mar. 7, 2013 and entitled "DYNAMIC REPORT BUILDING"; U.S. application Ser. No. 13/789,341 filed on Mar. 7, 2013 and entitled "REPORTING MODULES"; and U.S. application Ser. No. 13/790,281 filed on Mar. 8, 2013 and entitled "SYSTEMS AND METHODS FOR MANAGING GLYCEMIC VARIABILITY".

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and 'one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method for improving blood glucose sensing using a glucose sensor, the method comprising:
   receiving a priori calibration distribution information obtained prior to a sensor session, the a priori calibration distribution information including probability information about combinations of sensitivity and baseline;
   receiving blood glucose sensor data from the glucose sensor during a sensing session for the glucose sensor, the blood glucose sensor data including at least one sensor data point; and
   calibrating, during the sensor session, the at least one sensor data point without relying exclusively on factory calibration, assumptions of blood glucose accuracy, or reference data, wherein calibrating includes:
      receiving one or more real-time inputs during the sensor session, each of the one or more real-time inputs being capable of influencing calibration of the glucose sensor;
      forming a posteriori calibration distribution information using a Bayesian approach and based on the one or more real-time inputs;
      converting, in real-time during the sensor session, the at least one sensor data point from the glucose sensor to calibrated sensor data based on the a posteriori calibration distribution information; and
      displaying an indication of the calibrated sensor data for the glucose sensor.

2. The method of claim 1, wherein the a priori calibration distribution information comprises information from previous calibrations of a particular sensor session and/or information obtained prior to sensor insertion.

3. The method of claim 1, wherein the a priori calibration distribution information comprises probability distributions for sensitivity (m), sensitivity-related information, baseline (b), or baseline-related information.

4. The method of claim 1, wherein the a priori calibration distribution information comprises a priori guidance or validation ranges.

5. The method of claim 1, wherein the one or more real-time inputs comprise data received or determined since a previous calibration process.

6. The method of claim 5, wherein the one or more real-time inputs comprises at least one of: internally-derived real-time data, externally-derived real-time data, and combinations of internally- and externally-derived real-time data.

7. The method of claim 1, wherein the one or more real-time inputs includes at least one type of information selected from the group consisting of: stimulus signal output of sensor; sensor data measured by the sensor indicative of a glucose concentration; sensor data indicative of glucose rate-of-change; temperature measurements; sensor data from multi-electrode sensors; sensor data generated by redundant sensors; sensor data generated by one or more auxiliary sensors; data representative of a pressure on sensor; data generated by an accelerometer; sensor diagnostic information; impedance; and certainty level.

8. The method of claim 1, wherein the one or more real-time inputs includes at least one type of information selected from the group consisting of: glucose concentration information obtained from a reference monitor; information related to meal; insulin dosing time and amounts; insulin estimates; exercise; sleep; illness; stress; hydration; and hormonal conditions.

9. The method of claim 1, wherein the one or more real-time inputs includes combinations of internally- and externally-derived real-time data including at least one type of information selected from the group consisting of: information gathered from population based data; glucose concentration of the host; error at calibration or error in matched data pair; site of sensor implantation specific relationships; time since sensor manufacture; exposure of sensor, while on shelf, to temperature, humidity, or external factors; a measure of noise in a glucose concentration signal; and a level of certainty.

10. The method of claim 1, further comprising determining a level of certainty associated with calibration information and/or calibrated sensor data.

11. The method of claim 1, wherein forming a posteriori calibration distribution information comprises at least one of: an adjustment of the a priori calibration distribution information or a creation of a new range or distribution information based on the one or more real-time inputs.

12. The method of claim 11, wherein an adjustment of the a priori calibration distribution information comprises shifting, tightening, or loosening the a priori calibration distribution.

13. The method of claim 1, wherein the calibration distribution information is selected from the group consisting of: sensitivity; change in sensitivity; rate of change of sensitivity; baseline; change in baseline, rate of change of baseline, baseline profile associated with the sensor; sensitivity profile associated with the sensor; linearity; response time; relationships between properties of the sensor; relationships between particular stimulus signal output; and patient specific relationships between sensor and sensitivity, baseline, drift, impedance, impedance/temperature relationship, site of sensor implantation.

14. The method of claim 1, further comprising providing output of calibrated sensor data.

15. The method of claim 1, wherein the method is implemented using a processor and a memory coupled to the processor.

16. A system for improving blood glucose sensing using a continuous glucose sensor, the system comprising sensor electronics configured to be operably connected to the continuous glucose sensor, the sensor electronics configured to:
   receive a priori calibration distribution information obtained prior to a sensor session, the a priori calibration distribution information including probability information about combinations of sensitivity and baseline;

receive blood glucose sensor data from the glucose sensor during the sensing session for the glucose sensor, the blood glucose sensor data including at least one sensor data point; and calibrate, during the sensor session, the at least one sensor data point without relying exclusively on factory calibration, assumption of blood glucose accuracy or reference data, wherein calibrate includes:

receive one or more real-time inputs during the sensing session, each of the one or more real-time inputs being capable of influencing calibration of the glucose sensor;

form a posteriori calibration distribution information using a Bayesian approach and using the one or more real-time inputs;

convert, in real-time during the sensor session, the at least one sensor data point to calibrated sensor data based on the a posteriori calibration distribution information; and display an indication of the calibrated sensor data for the glucose sensor.

17. The system of claim 16, wherein the sensor electronics comprise a processor module, the processor module comprising instructions stored in computer memory, wherein the instructions, when executed by the processor module, cause the sensor electronics to form the a posteriori calibration distribution information.

18. A system for improving blood glucose sensing using a glucose sensor, the system comprising:

means for receiving a priori calibration distribution information obtained prior to a sensor session, the a priori calibration distribution information including probability information about combinations of sensitivity and baseline;

means for receiving blood glucose sensor data from the glucose sensor during the sensing session for the glucose sensor, the blood glucose sensor data including at least one sensor data point; and means for calibrating, during the sensor session, the at least one sensor data point without relying exclusively on factory calibration, assumption of blood glucose accuracy or reference data, wherein the means for calibrating includes:

means for receiving one or more real-time inputs during the sensing session, each of the one or more real-time inputs being capable of influencing calibration of the glucose sensor;

means for forming a posteriori calibration distribution information using a Bayesian approach and based on the one or more real-time inputs;

means for converting, in real-time during the sensor session, the at least one sensor data point to calibrated sensor data based on the a posteriori calibration distribution information; and means for displaying an indication of the calibrated sensor data for the glucose sensor.

19. The system of claim 17, wherein the instructions, when executed by the processor module, cause the sensor electronics to adjust the a priori calibration distribution information to form the a posteriori calibration distribution information.

20. The system of claim 17, wherein the instructions, when executed by the processor module, cause the sensor electronics to form the a posteriori calibration distribution information by creating a new range or distribution information based on the one or more real-time inputs.

* * * * *

UNITED STATES PATENT AND TRADEMARK OFFICE
CERTIFICATE OF CORRECTION

PATENT NO. : 10,335,075 B2
APPLICATION NO. : 13/827119
DATED : July 2, 2019
INVENTOR(S) : Stephen J. Vanslyke It is certified that error appears in the above-identified patent and that said Letters Patent is hereby corrected as shown below:

On the Title Page

On page 2, Column 1, item (56), U.S. Patent Documents, Line 12, delete "Bohm" and insert -- Bohm et al. --, therefor.

In the Specification

In Column 6, Line 38, delete "is are" and insert -- is --, therefor.

In Column 7, Line 60, delete "mg/dl" and insert -- mg/dL --, therefor.

In Column 12, Line 37, delete "(BR)" and insert -- (IIR) --, therefor.

In Column 22, Line 34, delete "calibration" and insert -- calibration. --, therefor.

In Column 24, Line 30, delete "an" and insert -- and --, therefor.

In Column 33, Line 48, delete "may be may be" and insert -- may be --, therefor.

In Column 34, Line 11, delete "an the" and insert -- the --, therefor.

In Column 34, Line 65, delete "illustrates" and insert -- Illustrates --, therefor.

Signed and Sealed this
Nineteenth Day of November, 2019

Andrei Iancu
*Director of the United States Patent and Trademark Office*